(12) United States Patent
Nordman et al.

(10) Patent No.: US 9,410,889 B2
(45) Date of Patent: Aug. 9, 2016

(54) METHOD AND SYSTEM FOR MULTIPLEX GENETIC ANALYSIS

(75) Inventors: Eric S. Nordman, Palo Alto, CA (US);
Mark F. Oldham, Los Gatos, CA (US);
Timothy Woudenberg, Moss Beach, CA (US)

(73) Assignee: Applied Biosystem, LLC, Carlsbad, CA (US)

( * ) Notice: Subject to any disclaimer, the term of this patent is extended or adjusted under 35 U.S.C. 154(b) by 1380 days.

(21) Appl. No.: 11/423,403

(22) Filed: Jun. 9, 2006

(65) Prior Publication Data

US 2010/0261158 A1 Oct. 14, 2010

Related U.S. Application Data

(60) Provisional application No. 60/689,692, filed on Jun. 10, 2005.

(51) Int. Cl.
*C12Q 1/68* (2006.01)
*G01N 21/64* (2006.01)

(52) U.S. Cl.
CPC ............ *G01N 21/648* (2013.01); *C12Q 1/6869* (2013.01); *G01N 21/6452* (2013.01)

(58) Field of Classification Search
None
See application file for complete search history.

(56) References Cited

U.S. PATENT DOCUMENTS

| | | | |
|---|---|---|---|
| 3,715,585 A | | 2/1973 | Harrick |
| 5,445,934 A | * | 8/1995 | Fodor et al. ...................... 506/16 |
| 5,538,613 A | * | 7/1996 | Brumley et al. ............... 204/612 |
| 5,632,957 A | | 5/1997 | Heller et al. |
| 5,633,724 A | | 5/1997 | King et al. |
| 5,993,634 A | * | 11/1999 | Simpson et al. .............. 204/612 |
| 6,127,129 A | | 10/2000 | Corn et al. |
| 6,236,778 B1 | * | 5/2001 | Laughlin ......................... 385/24 |
| 6,327,410 B1 | * | 12/2001 | Walt et al. ..................... 385/115 |
| 6,596,238 B1 | | 7/2003 | Belder et al. |
| 6,602,702 B1 | | 8/2003 | McDevitt et al. |
| 6,707,958 B2 | * | 3/2004 | Pering et al. ..................... 385/12 |
| 6,720,587 B2 | * | 4/2004 | Nozawa et al. ............... 257/184 |

(Continued)

FOREIGN PATENT DOCUMENTS

| | | |
|---|---|---|
| WO | WO-00/00975 | 2/2000 |
| WO | WO-00/53805 | 9/2000 |

OTHER PUBLICATIONS

Defintion of "total internal reflection" provided by the online dictionary at techweb.net.*

(Continued)

*Primary Examiner* — Robert T Crow

(57) ABSTRACT

The present disclosure provides apparatus, systems and method for detecting separately and substantially simultaneously light emissions from a plurality of localized light-emitting analytes. A system according to exemplary embodiments of the present disclosure comprises a sample holder having structures formed thereon for spatially separating and constraining a plurality of light-emitting analytes each having a single nucleic acid molecule or a single nucleic acid polymerizing enzyme, a light source configured to illuminate the sample holder, an optical assembly configured to collect and detect separately and substantially simultaneously light emissions associated with the plurality of light emitting analytes. The system may further include a computer system configured to analyze the light emissions to determine the structures or properties of a target nucleic acid molecule associated with each analyte.

29 Claims, 27 Drawing Sheets

(56) References Cited

U.S. PATENT DOCUMENTS

| | | | |
|---|---|---|---|
| 2001/0035991 A1* | 11/2001 | Hobbs et al. | 359/35 |
| 2002/0012930 A1* | 1/2002 | Rothberg et al. | 435/6 |
| 2002/0034757 A1 | 3/2002 | Cubicciotti | |
| 2002/0171079 A1 | 11/2002 | Braun et al. | |
| 2003/0040000 A1 | 2/2003 | Connolly et al. | |
| 2003/0044781 A1 | 3/2003 | Korlach et al. | |
| 2003/0082604 A1 | 5/2003 | Swanson et al. | |
| 2003/0095764 A1* | 5/2003 | Pering et al. | 385/120 |
| 2003/0174992 A1 | 9/2003 | Levene et al. | |
| 2003/0175773 A1* | 9/2003 | Chee et al. | 435/6 |
| 2003/0186310 A1 | 10/2003 | Kincaid | |
| 2004/0018491 A1* | 1/2004 | Gunderson et al. | 435/6 |
| 2004/0023247 A1* | 2/2004 | Xu et al. | 435/6 |
| 2004/0052489 A1* | 3/2004 | Duveneck et al. | 385/130 |
| 2004/0052729 A1* | 3/2004 | Penades et al. | 424/1.73 |
| 2004/0079893 A1 | 4/2004 | Dietz et al. | |
| 2004/0116279 A1 | 6/2004 | Addiego et al. | |
| 2004/0248144 A1* | 12/2004 | Mir | 435/6 |
| 2005/0001914 A1* | 1/2005 | Kueny | 348/294 |
| 2005/0112548 A1* | 5/2005 | Segawa et al. | 435/4 |
| 2006/0060766 A1 | 3/2006 | Turner et al. | |
| 2006/0068490 A1 | 3/2006 | Tang et al. | |
| 2009/0305287 A1 | 12/2009 | Nordman et al. | |
| 2009/0305908 A1 | 12/2009 | Nordman et al. | |
| 2009/0305909 A1 | 12/2009 | Nordman et al. | |

OTHER PUBLICATIONS

Pammer et al, ChemPhysChem, 2005, vol. 6, pp. 900-903 (plus Supplemental Material); published online Apr. 22, 2005.*
Levene et al, Science, vol. 299, pp. 682-686, published Jan. 31, 2003.*
Mark et al, Langmuir, 2004, vol. 20, pp. 6808-6817, published on the web Jun. 29, 2004.*
Defintion of "total internal reflection" provided by the online dictionary at techweb.net, 2008.*
International Search Report for Int'l Appl. No. PCT/US06/22545 dated Sep. 15, 2008; Along with the Written Opinion of the International Searching Authority.
Extended European Search Report for European Application No. 06784712.9 mailed Oct. 20, 2010, 7 pages.
Dontha, N. et al., "Generation of Biotin/Avidin/Enzyme Nanostructures with Maskless Photolithography", *Anal. Chem*, vol. 69(14), 1997, pp. 2619-2625.
EP10162890.7, ,"Partial European Search Report", Mailed Oct. 6, 2011, 2011, pp. 1-10.
Hengsakul, M et al., "Protein Patterning with a Photoactivatable Derivative of Biotin", *Bioconjugate Chem.*, 7, 1996, pp. 249-254.
Nordman, E et al., "New Optical Design for Automated DNA Sequencer", *Proc. SPIE.*, vol. 2680, 1996, 290-293.

* cited by examiner

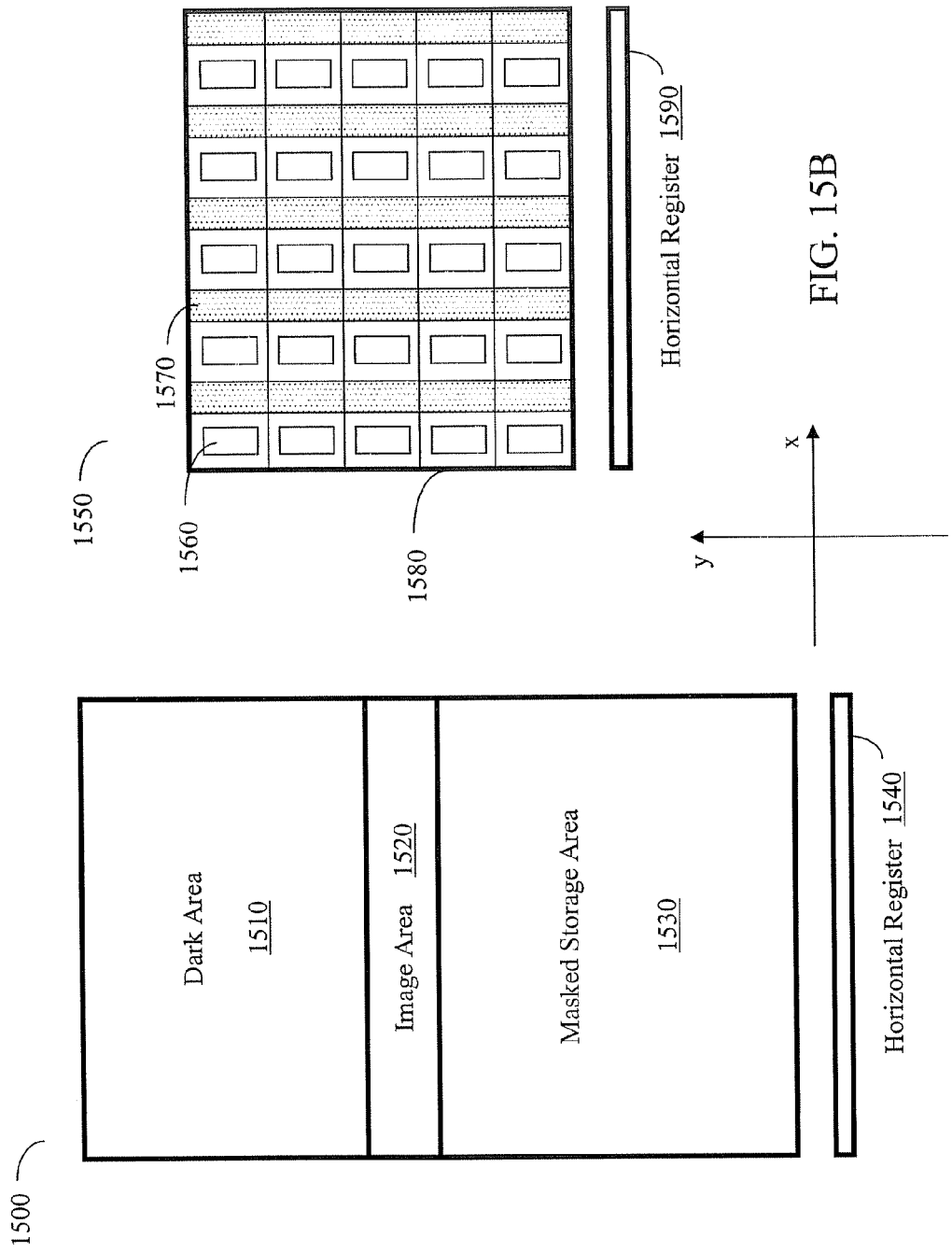

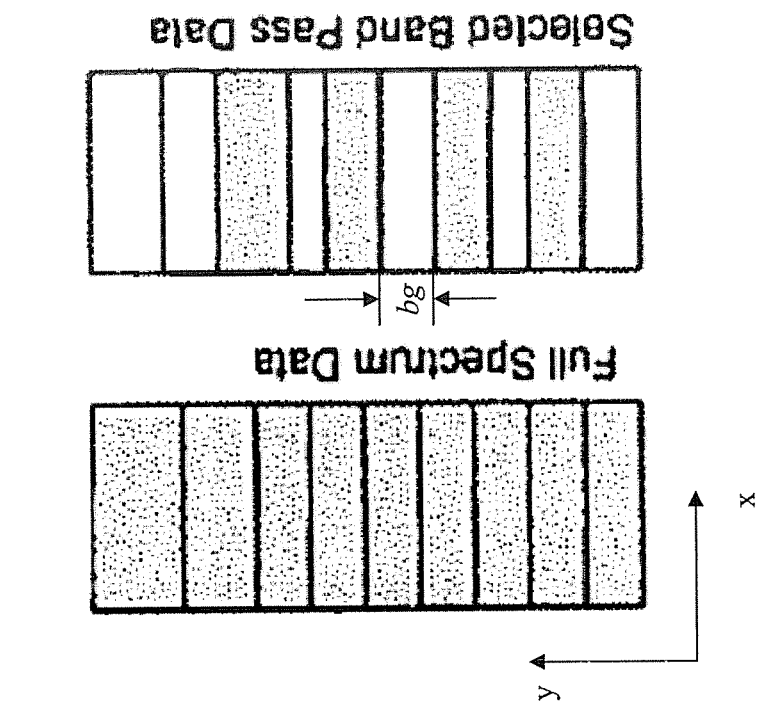
FIG. 16B
FIG. 16C
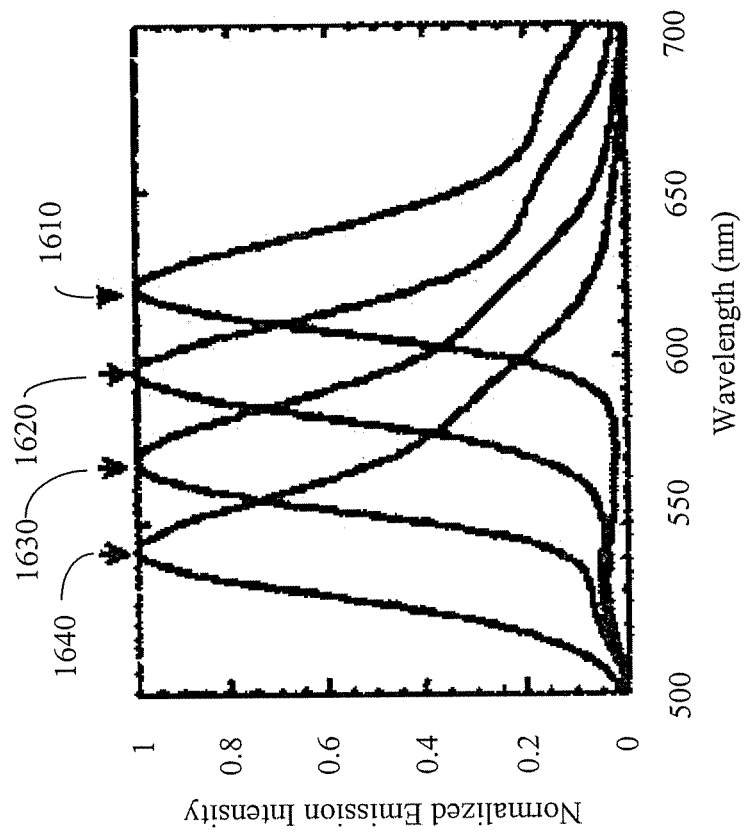
FIG. 16A

FIG. 17B

| Source Point Thruput (Bold items are adjustable) | | |
|---|---|---|
| CCD Specifications | | |
| Horizontal Pixels = | 512 | |
| Vertical Pixels = | 512 | |
| Readout Time = | 1.00E-07 | sec |
| Vertical shift Time = | 4.00E-07 | sec |
| Horiz Reg Clear Time = | 5.00E-06 | sec |
| | | |
| Source Point Image | | |
| Pitch between source points ($p$) = | 4 | pixels |
| Buffer rows ($d$) cleared = | 8 | rows |
| Bin color = | 3 | |
| Colors Read = | 4 | |
| Gap rows cleared = | 2 | rows |
| Bin gap or band gap ($bg$) = | 2 | rows |
| Source Point Gap ($g$) = | 4 | rows |
| Rows of source points = | 4 | |
| | | |
| Readout Time per source point = | 0.000241 | sec |
| Readout Time = | 0.0009656 | |
| # Source points = | 512 | |
| % good = | 25% | |
| # good source points = | 128 | |
| | | |
| Polymerase Rate = | 100 | bp/sec |
| Thruput = | 1105.92 | Mbp/day |
| | | |
| Data rate = | 530240 | Bytes/sec |
| | | |
| Number of rows/read = | 128 | |

FIG. 17C

| Source Point Thruput (Bold items are adjustable) | | |
|---|---|---|
| CCD Specifications | | |
| Horizontal Pixels = | 1004 | |
| Vertical Pixels = | 1002 | |
| Readout Time = | 2.86E-08 | sec |
| Vertical shift Time = | 5.00E-07 | sec |
| Horiz Reg Clear Time = | NA | sec |
| | | |
| Source Points Image | | |
| Pitch between source points ($p$) = | 4 | pixels |
| Buffer rows ($d$) cleared = | 8 | rows |
| Bin color = | 6 | |
| Colors Read = | 4 | |
| Gap rows cleared = | 4 | rows |
| Bin gap or band gap ($bg$) = | 4 | rows |
| Source Point Gap ($g$) = | 8 | rows |
| Rows of source points = | 4 | |
| Clear = | 2.87E-05 | sec |
| | | |
| Readout Time per source point = | 0.000282171 | sec |
| Readout Time = | 0.001132686 | |
| # source points = | 1004 | |
| % good = | 25% | |
| # good source points = | 251 | |
| | | |
| Polymerase Rate = | 100 | bp/sec |
| Thruput = | 2168.64 | Mbp/day |
| | | |
| Data rate = | 886389 | Bytes/sec |
| | | |
| Number of rows/read = | 224 | |

METHOD AND SYSTEM FOR MULTIPLEX GENETIC ANALYSIS

CROSS REFERENCE TO RELATED APPLICATIONS

This application claims a priority benefit under 35 U.S.C. §119(e) from U.S. Provisional Application No. 60/689,692 filed Jun. 10, 2005, which is incorporated herein by reference.

FIELD

The present application relates to molecular analysis, and more particularly to methods and systems for multiplex genetic analysis of single molecule nucleic acid synthesis.

INTRODUCTION

The information stored in a DNA molecule depends on particular sequences of nucleotides, which are bases or building blocks of the DNA molecule. DNA sequencing allows the determination of the nucleotide sequence of a particular DNA segment. A conventional method of DNA sequencing starts with a defined fragment of a DNA molecule as a template. Based on this template, a population of molecules differing in size by one base of a known composition is generated. The population of molecules is then fractioned based on size using, for example, acrylamide or agarose gel electrophoresis of single-stranded DNA molecules. The base at the truncated end of each of the fractionated molecules is thereafter determined to establish the nucleotide sequence.

A sequencing method called dideoxy sequencing was developed by Fred Sanger. His method is based on DNA synthesis in the presence of dideoxy nucleotides (ddNTP), which differ from normal deoxynucleotides (dNTP) in that they lack a 3'-hydroxyl group so that once a dideoxy nucleotide is incorporated, it will terminate strand synthesis. The procedure for dideoxy sequencing starts with setting up four reactions each in a different tube containing the single strand DNA to be sequenced, labeled (tagged) primer, DNA polymerase, normal dNTPs, and a different ddNTP (i.e. for A, T, C, or G). A dideoxy nucleotide will be incorporated, randomly, at each point the corresponding nucleotide occurs in the template strand. Each time a dideoxy nucleotide is incorporated, it will stop further DNA replication. This will generate a set of fragments of various lengths, each fragment corresponding to the point at which there is a nucleotide complementary to the dideoxy nucleotide. The fragments are then separated based on their length by electrophoresis. With the smaller fragments migrating faster, the sequence can be determined by associating the base composition with each fragment.

The above technique for DNA sequencing suffer from the disadvantage that sample preparation is relatively complex in order to ensure that the tubes contain the same DNA molecules or fragments of the same DNA molecules to be sequenced. This leads to increased costs and the possibility of error. A simpler method results if molecule-based investigation techniques are used to observe the synthesis of a single DNA molecule. Because only one molecule is being observed, there is no need to ensure that all of the surrounding molecules are the same.

Specialized tools for imaging and spectroscopy have been developed to characterize nanomaterials and nanomaterials-related phenomenon. Techniques for constructing these tools comprise near-field scanning optical microscopy (NSOM) and single molecule spectroscopy (SMS). These techniques offer unique capabilities for investigating properties at the molecular level owing to their high spatial resolution, chemical sensitivity, and their ability to determine dynamical properties such as molecule binding/unbinding kinetics and the structural dynamics of polymers. For example, a sample-scanning confocal fluorescence microscope using SMS developed by McNeil et al. has demonstrated spatial resolution of ~400 nm, and single molecule sensitivity. It uses a detector system having a single-photon avalanche diode and a sensitive TE-cooled CCD spectrometer, permitting the ability to monitor fluorescence in the range of 400 to 1100 nm at a resolution of 20 nm and the ability to conduct time-lapse fluorescence spectroscopy with single molecule sensitivity.

The single-molecule techniques described above, however, often employ femtoliter-scale observation volumes and require the use of picomolar to nanomolar sample concentrations to ensure that on average only one molecule will be present in the sample volume. These concentrations are far lower than those that normally occur in nature. Thus, molecule dynamics that are affected by concentration cannot be suitably tested using the techniques. To overcome the deficiencies of NSOM and SMS techniques, other developments have been proposed. For example, Levene et al. describes a device for single molecule analysis employing a sample plate, which has 50 nm-diameter holes in a 100 nm thick aluminum film on a fused silica coverslip. When the holes are illuminated from under the fused silica coverslip, the holes act as zero-mode waveguides prohibiting the light from going through the aluminum film because the diameter of the holes are much smaller than the wavelength of the light, which is about 400-700 nm. The light, however, does generate an evanescent field that extends about 10 nm into the cavity of each illuminated hole producing a zeptoliter-scale effective observation volume near the opening of the hole. See Levene et al., US Patent Application Publication Number 2003/0174992 A1, which is incorporated herein by reference.

The small observation volume provided by the zero-mode waveguides described by Levene, however, raises other challenges spanning from sample preparation, signal detection, noise or background suppression, data collection and data analysis algorithms. Accordingly, significant further developments are needed.

The present teaching in one aspect comprises an affordable high-sensitivity and high-throughput system and method for single-molecule analysis that performs at a lower cost relative to conventional systems used in sequencing, resequencing, and SNP detection. These and other features of the present teaching are set forth herein.

SUMMARY

The present disclosure provides apparatus, systems and method for analyzing a plurality of molecules by detecting separately and substantially simultaneously light emissions from a plurality of localized light-emitting analytes each including a single one of the plurality of molecules. The detected light emissions, after being properly analyzed, can be used to deduce the structure or properties of each of the plurality of molecules. In some embodiments, the apparatus, systems and methods can be used for nucleic acid sequencing, nucleic acid resequencing, and/or detection and/or characterization of single nucleotide polymorphism (SNP analysis) including gene expression.

In various embodiments, the present invention can provide an apparatus for sequencing a plurality of target nucleic acid molecules including a sample holder configured to separate and confine a plurality of source points each including a single one of the target nucleic acid molecules, a fraction of a nucleic acid molecule, or a nucleic acid polymerizing enzyme molecule, a light source configured to direct excitation light toward the sample holder at an angle with respect to a normal of the sample holder, the excitation light illuminating the source points and causing the source points to fluoresce, at least one detector, and an optical assembly configured to collect fluorescent signals from illuminated source points to form images of the source points on the at least one detector.

In various embodiments, the present invention can provide a method for sequencing a plurality of target nucleic acid molecules, including subjecting a plurality of source points of a sample holder to nucleic acid polymerization reactions, wherein the source points each include fluorescence-labeled bases, primers, and at least one nucleic acid polymerizing enzyme molecule, and wherein the plurality of source points each has a single one of the target nucleic acid molecules, directing excitation light toward the sample holder at an angle with respect to a normal of the sample holder to illuminate the source points and to cause the source points to fluoresce, and collecting fluorescent signals from the illuminated source points and focusing the fluorescent signals onto at least one detector to form images of the source points on the at least one detector to determine time sequences of base incorporations in the polymerization reactions.

In various embodiments, the present invention can provide a method for sequencing a plurality of target nucleic acid molecules, including subjecting a plurality of source points of a sample holder to nucleic acid polymerization reactions, wherein the source points each include fluorescence-labeled bases, primers, and at least one of the target nucleic acid molecules, and wherein the plurality of source points each has a single nucleic acid polymerizing enzyme molecule, directing excitation light toward the sample holder at an angle with respect to a normal of the sample holder to illuminate the source points and to cause the source points to fluoresce, and collecting fluorescent signals from the illuminated source points and focusing the fluorescent signals onto at least one detector to form images of the source points on the at least one detector to determine time sequences of base additions in the polymerization reactions.

In various embodiments, the present invention can provide a method for sequencing a plurality of target nucleic acid molecules, including enriching a sample holder with a plurality of source points each having a single one of the target nucleic acid molecules and/or a single nucleic acid polymerizing enzyme molecule, subjecting the plurality of source points to nucleic acid polymerization reactions, (1) wherein when the source points have a single one of the target nucleic acid molecules, the source points each further include fluorescence-labeled bases, primers, and at least one nucleic acid polymerizing enzyme molecule, (2) wherein when the source points have a single nucleic acid polymerizing enzyme molecule, the source points each further include fluorescence-labeled bases, primers, and at least one of the target nucleic acid molecules, and (3) wherein when the source points have a single one of the target nucleic acid molecules and a single nucleic acid polymerizing enzyme molecule, the source points each further include fluorescence-labeled bases and primers, directing excitation light toward the sample holder at an angle with respect to a normal of the sample holder to illuminate the source points and to cause the source points to fluoresce, and collecting fluorescent signals from the illuminated source points and focusing the fluorescent signals onto at least one detector to form images of the source points on the at least one detector to determine time sequences of base incorporations in the polymerization reactions.

A system according to exemplary embodiments of the present disclosure comprises a sample holder having structures formed thereon for spatially separating and constraining a plurality of light-emitting analytes each having a single one of the plurality of molecules to be analyzed. In exemplary embodiments, each of the plurality of molecules is a single nucleic acid molecule, a fraction of the nucleic acid molecule, an oligonucleotide molecule, or a single nucleic acid polymerizing enzyme. The system further comprises a light source configured to illuminate the sample holder, an optical assembly configured to collect and detect separately and substantially simultaneously light emissions associated with the plurality of light emitting analytes. The system may further include a computer system configured to analyze the light emissions to determine the structures or properties of a target nucleic acid molecule associated with each analyte.

In one exemplary embodiment of the present invention, the light source is configured to produce excitation light that is directed toward the sample holder at an angle with respect to a normal of a plane associated with the sample holder. In further embodiments, excitation light is directed toward the sample holder such that total internal reflection occurs and the excitation light is recycled multiple times before exiting the sample holder.

In one exemplary embodiment of the present invention, the optical assembly comprises at least one pixilated sensor device such as a charge coupled device (CCD) detector or CMOS detector configured to detect substantially simultaneously light emissions from the multiple localized light-emitting analytes. In further embodiments, the optical assembly is configured to disperse spectrally the light emitted from the multiple localized light-emitting analytes onto the detector(s) so that different frequency bands of the emitted light are detected by different areas of the detector(s).

These and other features of the present teaching are set forth herein.

BRIEF DESCRIPTION OF THE DRAWINGS

The skilled artisan will understand that the drawings, described below, are for purposes of illustration only, and are not intended to limit the scope of the present teaching in any way.

FIG. 15A is a block diagram illustrating a frame transfer CCD array in a detector in the system in FIG. 1 according to exemplary embodiments of the present teaching.

FIG. 15B is a block diagram illustrating an interline CCD array in the detector in the system in FIG. 1 according to exemplary embodiments of the present teaching.

FIG. 16A are examples of normalized fluorescent spectra corresponding to four different fluorescent dyes.

FIG. 16B is a block diagram illustrating full spectrum data.

FIG. 16C is a block diagram of the full spectrum data with the most informative wavelengths distinguished from less informative wavelengths.

FIGS. 17B-17C are each a spreadsheet for estimating the throughput of reading out data from a CCD array using the method in FIG. 17A.

DESCRIPTION OF VARIOUS EMBODIMENTS

It is to be understood that both the foregoing summary and the following description of various embodiments are exemplary and explanatory only and are not restrictive of the present teachings. In this application, the use of the singular comprises the plural unless specifically stated otherwise. Also, the use of "or" means "and/or" unless stated otherwise. Similarly, "comprise," "comprises," "comprising," "comprise," "comprises," and "including" are not intended to be limiting.

Additionally, while certain embodiments are described in detail herein, particularly embodiments suitable for analysis of single molecule nucleic acid synthesis, it is to be understood the apparatus, systems and methods of the present disclosure may be employed in other applications for analysis of single molecules, such as but not limited to directed resequencing, SNP detection, and gene expression.

Furthermore, the figures in this application are for illustration purposes and many of the figures are not to scale with corresponding hardware. Many parts of the features in the figures in this application are drawn out of scale purposefully for ease of illustration.

Systems according to some embodiments of the present disclosure generally comprise a sample holder configured to hold a plurality of localized light-emitting analytes each comprising a single one of a plurality of molecules to be analyzed, a light source configured to illuminate the sample holder, and an optical assembly configured to collect and detect light emitted from the source points.

Figure 1:
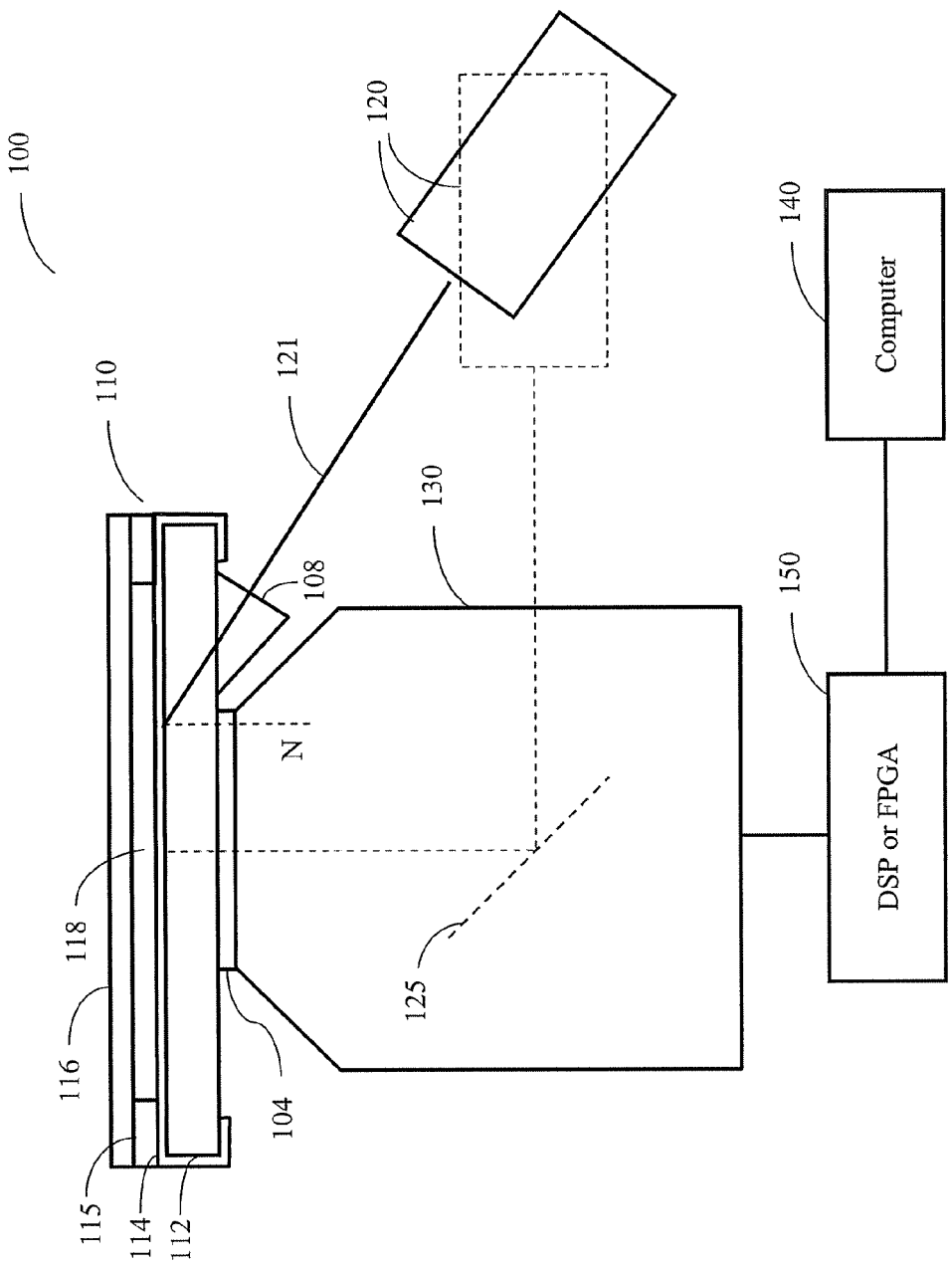
FIG. 1 is a block diagram of an exemplary embodiment of a high throughput system for single molecule analysis.

FIG. 1 is a block diagram of an exemplary embodiment of a system 100 for detecting and analyzing light emitted from the plurality of light-emitting analytes. As shown in FIG. 1, system 100 comprises a sample holder 110, a light source 120, and an optical assembly 130. System 100 may further comprise a host computer system 140 (see also FIG. 18) configured to analyze optical data detected by optical assembly 130. System 100 may also comprise one or more digital signal processors (DSP) or field programmable gate arrays (FPGA) 150 coupled between optical assembly 130 and host computer system 140. DSPs or FPGAs 150 can be used to execute algorithms for base determination, as explained in more detail below.

System 100 may optionally comprise an index-matching prism 108. A space between the sample holder 110 and the optical assembly 130 may be filled with a fluid 104. The utility of the index-matching prism 108 and the fluid 104 is discussed below. Although for reasons discussed below, it may be advantageous to direct the excitation light from the light source 120 to the sample holder 110 at an angle, as shown by the solid line 121 in FIG. 1, system 100 is not limited to such use, and the excitation light can be directed via a dichroic filter 125 toward the sample holder along a normal N of the sample holder 110, as shown by the dashed lines in FIG. 1.

In exemplary embodiments of the present teaching, sample holder 110 is configured to support and confine the plurality of light-emitting analytes. For ease of discussion, each localized light-emitting analyte will hereafter be referred to as a dye or a "source point". In various embodiments, a dye or a source point comprises a single nucleic acid molecule, a fraction of a nucleic acid molecule, an oligonucleotide molecule, or a single nucleic acid polymerizing enzyme. The dye or source point may also comprise one or more other molecules, constituents, or reactants. The emitted light from the complex can be used to deduce the structure or properties of a target nucleic acid molecule.

In one exemplary embodiment, in applications employing nucleic acid sequencing, each source point is a complex of a single nucleic acid polymerizing enzyme, a target nucleic acid molecule, and at least one incorporated or incorporating fluorescence-labeled nucleotide analog. The source point is localized or spatially constrained in at least one dimension that is less than the wavelength of the excitation light. The fluorescent label on the nucleotide analog emits fluorescent light upon illumination by light source 120. In exemplary embodiments of the present teaching, four different nucleotide analogs are labeled with four different fluorescent dyes each having a unique emission spectrum. The four different fluorescent dyes can also be associated with four different frequency bands each corresponding to a peak in emission intensity according to the respective spectrum. The four different frequency bands are hereafter referred to as first, second, third, and fourth frequency bands.

Thus, the time sequence of base incorporation can be observed by detecting fluorescent signals from sequentially incorporated nucleotide analogs associated with a source point. The fluorescent light signals from different source points on the sample holder 110 are substantially simultaneously collected and detected by optical assembly 130 and are analyzed by computer system 140 to determine the identities of the incorporated nucleic acid molecule in each of the source points. To reduce or eliminate interference between fluorescent signals associated with consecutive incorporation events on a same source point, after detection of an incorporation event, fluorescent label on the newly incorporated nucleotide can be bleached, cleaved or otherwise removed with a known technique. Photo-cleavable linkers may be utilized to facilitate efficient and consistent removal of the fluorescent labels.

In some embodiments, the source points are localized or spatially constrained at different locations on sample holder 110 by immobilizing the single nucleic acid molecule or the single nucleic acid polymerizing enzyme in each source point at one of the locations. This allows separate and substantially simultaneous detection of fluorescent emission from the plurality of source points. A conventional method or one of the methods discussed below can be used to immobilize the enzymes or the template nucleic acid molecules.

Figure 2:
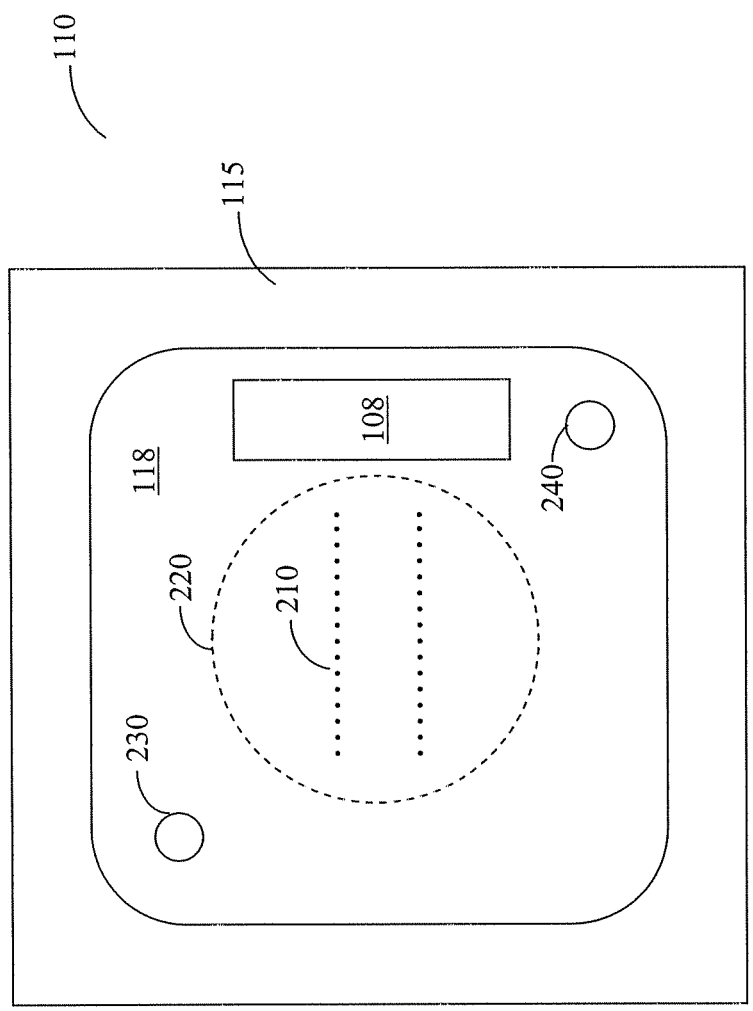
FIG. 2 is a top view of a sample holder in the system.

FIG. 2 is a block diagram of a top-down view of sample holder 110 according to exemplary embodiments. As shown in FIGS. 1 and 2, in exemplary embodiments, sample holder 110 comprises a substrate 112 made of a material transparent to the excitation light from light source 120 and to the fluorescent emissions from the source points. A metallic film 114 is formed on a top surface of substrate 112. Depending on specific applications, for reasons discussed below, metallic film 114 may extend to the side surfaces and edge portions of a bottom surface of the substrate 112, as shown in FIG. 1. Sample holder 110 may further comprise a sealer 115 and a cover 116 for evaporation control. A space 118 is formed between the cover 116 and the substrate 112, which space serves as a sample chamber for holding a sample fluid that supplies at least one of the constituents or reactants in each source point. In various embodiments, in applications of nucleic acid sequencing, the sample fluid comprises a fluorophore solution of different types of fluorescent-labeled nucleotides. Sample holder 110 may further comprise a fill hole 230 for filling the sample chamber 118 with the sample fluid and a drain hole 240 for draining the sample fluid from the sample chamber. Fill hole 230 and drain hole 240 are preferably located near two opposite corners of sample holder 110, as shown in FIG. 2, for more complete draining and washing away of sample fluid.

As shown in FIG. 2, sample holder 110 is configured to hold a plurality of spatially separated and constrained source points 210 in a field of view 220 of the optical assembly 130. The spatial separation and confinement of the source points 210 help in one aspect to detect light signals from the source points 210 separately and substantially simultaneously. Although FIG. 2 shows that the source points 210 on the sample holder 110 are arranged in an array having two rows and a number of columns, such arrangement is not necessary as long as the source points are sufficiently spaced from each other so that the light signals from them can be effectively resolved by optical assembly 130 When the source points are arranged in an array, the array may be perfect, meaning each array element site has an immobilized functional source point, or imperfect, meaning at least one array element site is missing a source point, has a source point that is not functional, or has multiple source points that are too close together to allow resolution by the optical assembly 130.

Figure 3:
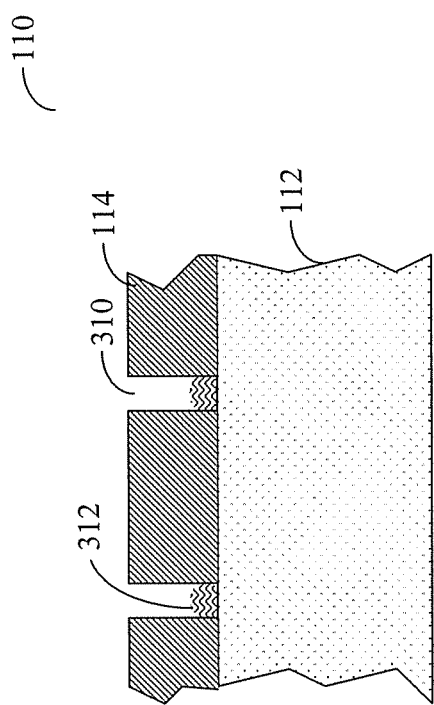
FIG. 3 is a cross-sectional view of a portion of the sample holder.

In various embodiments, the metallic film 114 on the top surface of the substrate 112 has etched patterns forming cavities for housing the plurality of source points and separating the plurality of source points to allow resolution by the optical assembly 130. In some embodiments, zero-mode waveguides, such as those described in Patent Application Number US 2003/0174992 by Levene et al, which is incorporated herein by reference, are formed in metallic film 114, as shown in a cross-sectional view in FIG. 3. Zero-mode waveguides are known in the art and can be created using a variety of materials and methods. As a specific, non-limiting example, substrate 112 is a fused silica substrate, metallic film 114 is an aluminum film formed on the fused silica substrate, and an array of holes 310 are formed by masking and plasma etching the aluminum film to create holes 310 in the aluminum film. Each hole 310 has a diameter that is substantially smaller than a wavelength of the excitation light from light source 120 and a depth that is sufficient to block transmission of the excitation light through the hole. Thus, each hole 310 acts as a zero-mode waveguide for the excitation light from light source 120, allowing the excitation light, which comes to the waveguides from the substrate side, to penetrate only a bottom portion 312 of the hole 310. At the same time, the zero-mode waveguides also serves to block light emitted or scattered from the sample fluid on the sample holder 110 except emissions coming from any light emitting agents immobilized in the bottom portions 312 of the waveguides or diffusing past the bottom portions 312 of the waveguides.

Thus, in some embodiments, to allow the detection and analysis of light emitted from the source points 210, each source point 210 is immobilized in the bottom portion 312 of a zero-mode waveguide 310, so that light emitted from the source point can escape the hole 310, pass through substrate 112 and be collected by optical assembly 130. Preferably, only one source point should be present in the bottom portion 310 of a hole 310 because it would be difficult for the optical assembly to distinguish the emitted light from more than one source point in a single hole 310 considering the size of the hole. Therefore, in the exemplary embodiment, holes 310 that either do not have any source point immobilized in the bottom portion 312 or have more than one source point immobilized in the bottom portion 312 do not contribute to the analysis and are considered as empty sites in an array of source points 210.

For ease of discussion, the description hereafter will be illustrated in the context of nucleic acid sequencing, while the methods, systems and apparatus of the present teaching can be applied to other types of molecular analysis. Methods of immobilizing molecules involved in a genetic assay in waveguides 310 are described in detail in US Patent Application Number US 2003/0044781 by Korlach et al., which is incorporated herein by reference. Using the methods described by Korlach, some of the array of holes 310 can each contain a single DNA molecule or enzyme immobilized in the bottom portion 312, while a large percentage of the holes may contain none or multiple molecules in each of them and are thus useless in the analysis.

Figure 4:
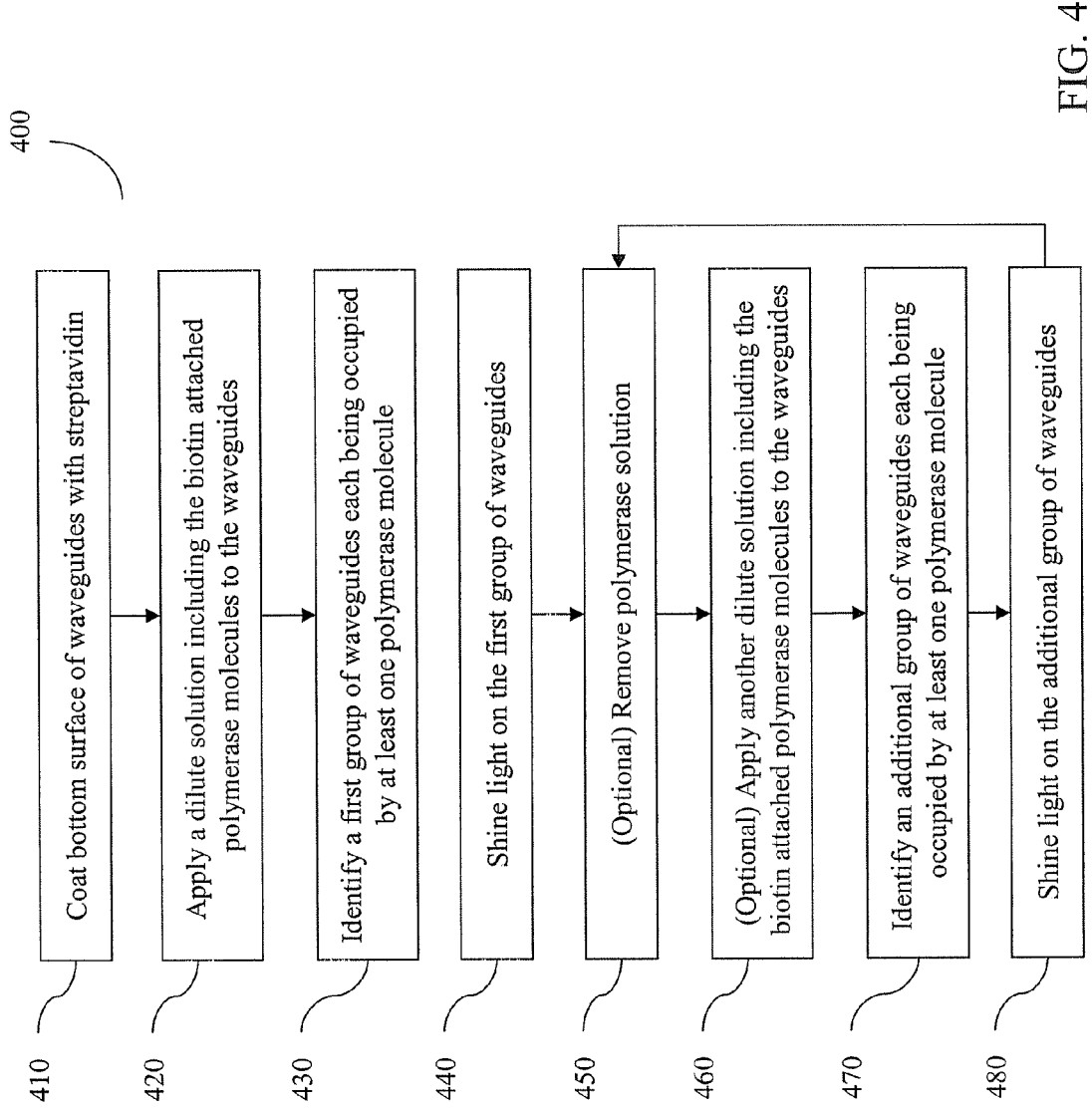
FIG. 4 is a flowchart illustrating an exemplary embodiment of a method useful for enriching the sample holder with a plurality of spatially restrained source points.

FIG. 4 illustrates a flowchart of one embodiment of a method 400 for enriching the sample holder 110 with source points. Method 400 increases the efficiency and throughput of system 100 by maximizing the percentage of holes 310 that have in each of them a single source point in the bottom portion 312. As shown in FIG. 4, according to exemplary embodiments of the present teaching, method 400 comprises the following steps: step 410 in which uncovered portions of the substrate 112 are coated with streptavidin, step 420 in which a dilute solution including a plurality of molecules each being a nucleic acid molecule or a nucleic acid polymerizing enzyme is applied to the waveguides 310. Each of the plurality of molecules has a photoactivatable biotin attached to it. The concentration of the plurality of molecules in the solution is selected to be lower than the optimal Poisson distribution so that when the solution is applied to the waveguides 310 on the sample holder 110, most of the waveguides 310 would be populated by zero number of the molecules and that statistically few of the waveguides 310 would be occupied by more than one of the molecules.

Still referring to FIG. 4, method 400 further comprises step 430 in which a first group of waveguides are identified as each being occupied by at least one nucleic acid molecule or a nucleic acid polymerizing enzyme. The first group of waveguides can be identified by using, for example, a simplified sequencing assay. Method 400 further comprises step 440 in which light is shown on each of the first group of waveguides. The light activates the biotin attachment in those waveguides and thus immobilizes the molecules using the biotin-streptavidin bound. Step 440 is followed by an optional step 450 in which the solution is removed from the sample holder by washing or inactivation, leaving only those molecules bonded to the bottom of the waveguides. Step 450 is followed by an optional step 460 in which another dilute solution of the biotin attached molecules are applied to the waveguides 310 on sample holder 110. Method 400 further comprises step 470 in which an additional group of waveguides are identified as each being occupied by at least one nucleic acid molecule or a nucleic acid polymerizing enzyme. In one embodiment, the additional group of waveguides do not overlap with previously identified group(s) of waveguides. Method 400 further comprises step 480 in which light is shown on each of the additional group of waveguides and thus immobilizes the nucleic acid molecules or enzymes in the additional group of waveguides. Method 400 then repeats steps 450-480 until most of the waveguides are populated by bound molecules. Note that steps 450 and 460 are optional because, instead of carrying out steps 450 and 460, one can simply wait for a period of time to allow more of the plurality of molecules to diffuse into some of the waveguides.

Optionally, after populating the waveguides with polymerase molecules, a primer is attached to each polymerase molecule by a flexible linker. Attaching the primer to the polymerase molecule helps the analysis because the DNA template would be tethered and not float away, allowing subsequent synthesis to occur on the same template. In one aspect, this benefits the analysis by increasing read lengths and throughput. Longer read lengths help to simplify any fragment assembly problem.

Figure 5:
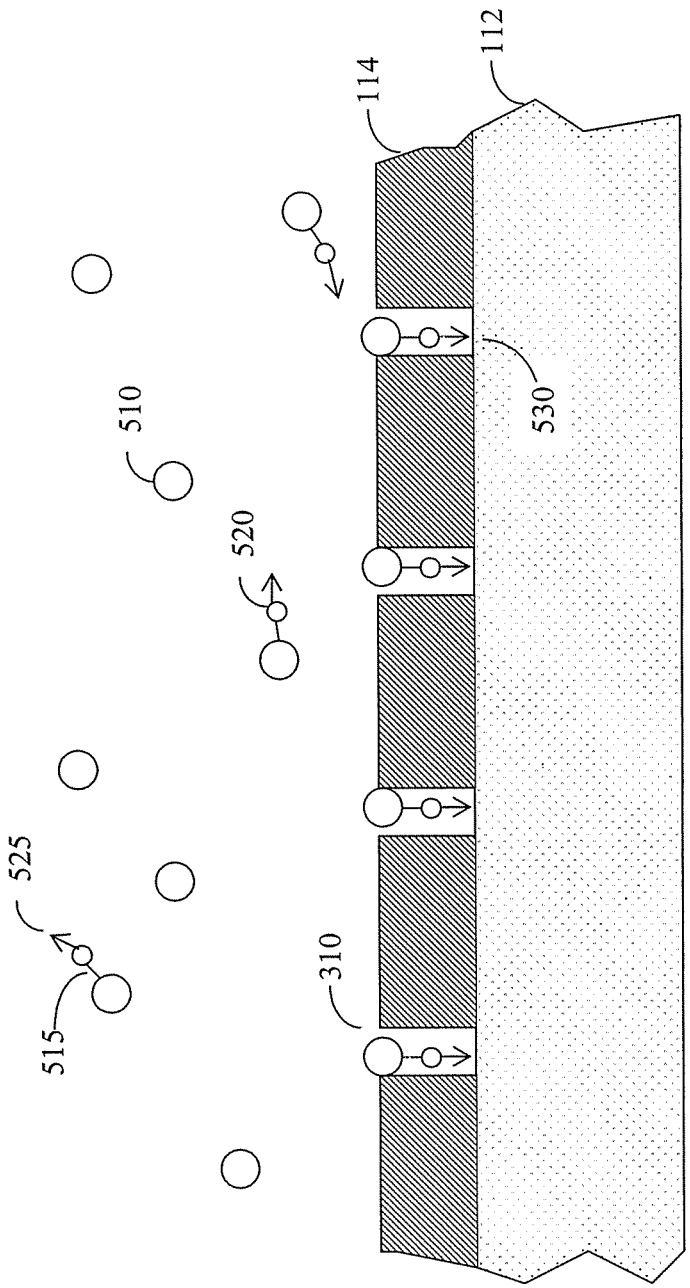
FIG. 5 is a diagram illustrating further embodiments of a method useful for enriching the sample holder with a plurality of spatially constrained source points.

In some embodiments, a method for enriching the sample holder involves the use of nanobeads. As shown in FIG. 5, the sample fluid comprise nanobeads 510, and the enzyme or nucleic acid molecule 520 is attached to a nanobead 510 by a cleavable linker 515, in a manner that most of the nanobeads in the sample fluid each have at most one enzyme or nucleic acid molecule attached. The nanobeads are sized such that only one nanobead is likely to fit in a waveguide 310. The enzyme or nucleic acid molecule 520 has a photoactivatable linker 525 that allows attachment of the composite including the nanobead, the nucleic acid molecule or enzyme, and the cleavable linker 515 to an attachment site 530 at the bottom of a waveguide 310. The attachment is activated by shining light from the bottom of substrate 112. Since only those nanobeads each having an enzyme or nucleic acid molecule with the photoactivatable linker can bind to the substrate 312, the presence of a nanobead in a waveguide 310 excludes other enzyme or nucleic acid molecules from diffusing into the same waveguide, there is no need to determine which waveguides are occupied by the nanobeads before shining light on the waveguides to activate the linkers 525. The shining of light can be repeated later when more nanobeads with enzyme or nucleic acid molecules attached thereon diffuse into other waveguides. Thus, the nanobeads can be used to increase the number of waveguides each having a single nucleic acid molecule or enzyme attached therein. After binding, the nanobeads are removed from the enzyme or nucleic acid molecules by, for example, chemically cleaving the linkers 515 or dissolving the nanobeads.

Figure 6:
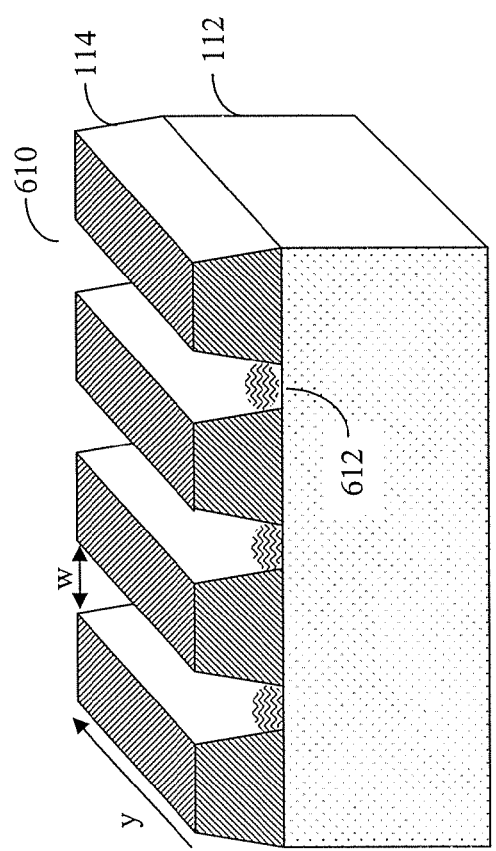
FIG. 6 is a 3-dimensional view of a portion of the sample holder according to further embodiments of the present teaching.

In alternative embodiments of the present teaching, sample holder 110 comprises slots or channels to facilitate confining the plurality of source points 210 on the sample holder 110. FIG. 6 illustrates a 3-dimensional view of a plurality of channels 610 formed in metallic film 114 on substrate 112. As a non-limiting example, channels 610 are formed in an aluminum film over a fused silica substrate. Each channel 610 has a width w that is smaller than a wavelength associated with light source 120. In exemplary embodiments of the present teaching, light from light source 120 is linearly polarized and the polarization direction is oriented with the electric field vector in the light wave along the width direction of the channels. Thus, only a bottom portion 612 in each channel 610 would be illuminated by the excitation light from light source 120, as shown in FIG. 6. Channels 610 can be formed using conventional techniques, such as conventional semiconductor processing or integrated circuit (IC) fabrication techniques.

Figure 7:
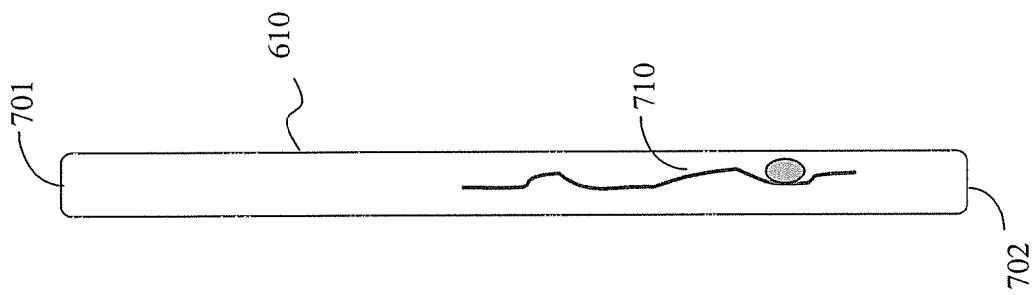
FIG. 7 is a diagram illustrating a DNA sequencing process along a channel on the sample holder according to exemplary embodiments of the present teaching.

Sample holder 110 with channels 610 formed thereon has multiple advantages over a sample holder with zero-mode waveguide holes 310 formed thereon. Because the fluorescent emissions are largely unpolarized, they would not be attenuated when they try to exit the channels 610 as much as when they try to exit holes 310 of sub-wavelength dimension. So, more emitted light from sample holder 110 can be collected and detected by optical assembly 130, resulting in increased signal to noise ratio. In addition, each channel 610 can house a larger DNA template molecule if the DNA molecule is oriented parallel to the channel, as shown in a top-down view of the channel in FIG. 7. This way, the polymerase can migrate down the template for a much longer distance without exiting the illuminated volume 612. The DNA molecule can be tethered so that it can remain in one location while the polymerase, having a finite processivity, may fall off the template and be replaced by another polymerase. This can lead to longer read lengths and thus significantly simplified assembly processes, especially during denovo sequencing. Although FIG. 7 shows that channel 610 is closed at both ends 701 and 702, the channels 610 on sample holder can be open on either or both ends by extending all the way to the edge(s) of the sample holder, as shown in FIG. 8C below.

The polymerase or template molecules can be attached to sample holder 110 using conventional photoactivatable linkers. In exemplary embodiments of the present teaching, channels 610 may house more than one polymerase or template molecules attached to sample holder 110 by flexible linkers that are placed in the channels 610. The molecules should be attached to the channels 610 in a resolvable fashion, meaning that they are sufficiently spaced from each other to allow efficient resolution of the emissions therefrom by the optical assembly 130.

Figure 8A:
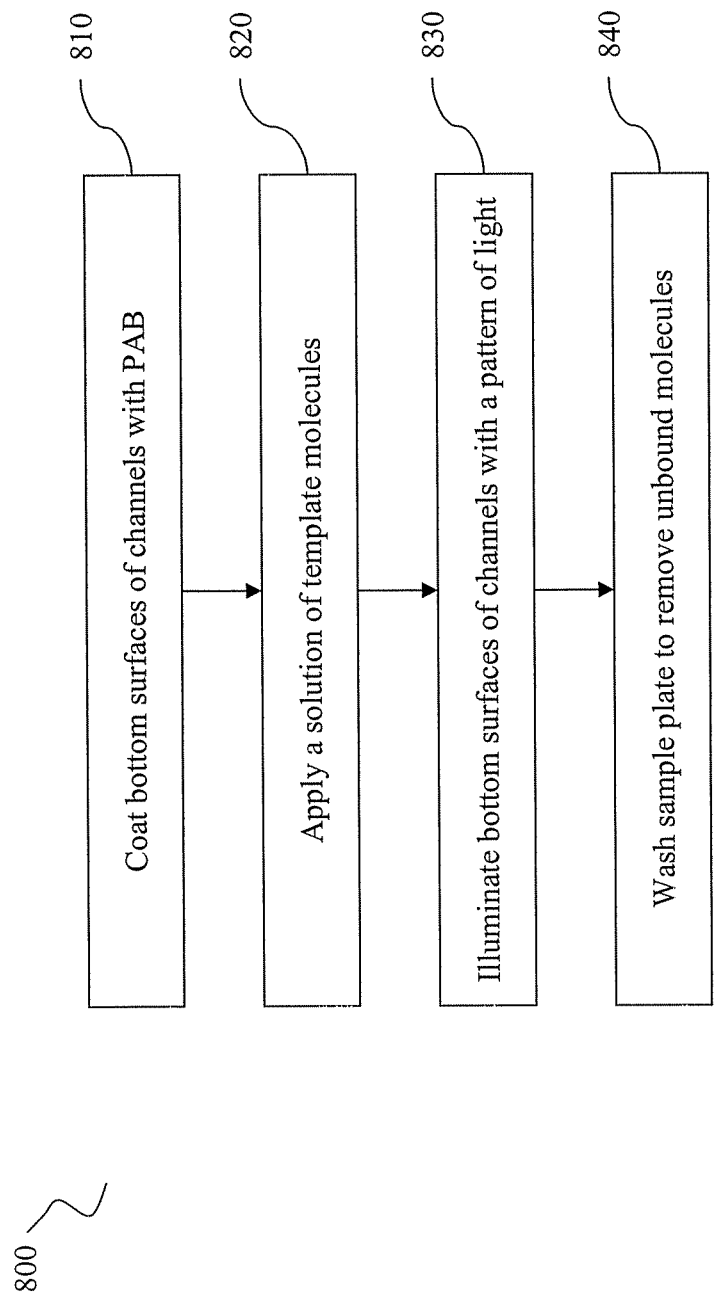
FIGS. 8A and 8B are flowcharts illustrating further embodiments of a method useful for placing a plurality of source points on the sample holder in FIG. 6.

FIG. 8A illustrates a method 800 for enriching the sample holder 110 with source points by attaching the polymerase or template molecules in channels 610 in a resolvable fashion according to exemplary embodiments of the present teaching. As shown in FIG. 8A, method 800 comprises step 810 in which exposed portions of the top surface of the substrate 112 are coated with a photoactivatable linking substance such as PHOTOACTIVATABLE BIOTIN™ (PAB), step 820 in which a solution of enzyme or template molecules is applied to sample holder 110, and step 830 in which the PAB is exposed to a pattern of light shone from the bottom surface of the substrate 112. The pattern of light may be created by interference or refraction using grating or other conventional techniques and has interleaving lighted and dark areas in each channel 610. The distance between two neighboring lighted areas is selected based on the resolution of the optical assembly 130 so that emissions from the two lighted areas can be separately and substantially simultaneously detected by the optical assembly 130. The PAB in the lighted area will be activated causing the template molecules to be attached to the sample holder in those areas, while the PAB in the dark areas will not be activated so no template molecules will be attached to those areas. Method 800 further comprises step 840 in which sample holder 110 is washed to remove unbound template molecules, leaving the bound enzyme or nucleic acid molecules in each channel 610 and allowing the formation of optically resolvable source points 210 on sample holder 110.

Figure 8B:
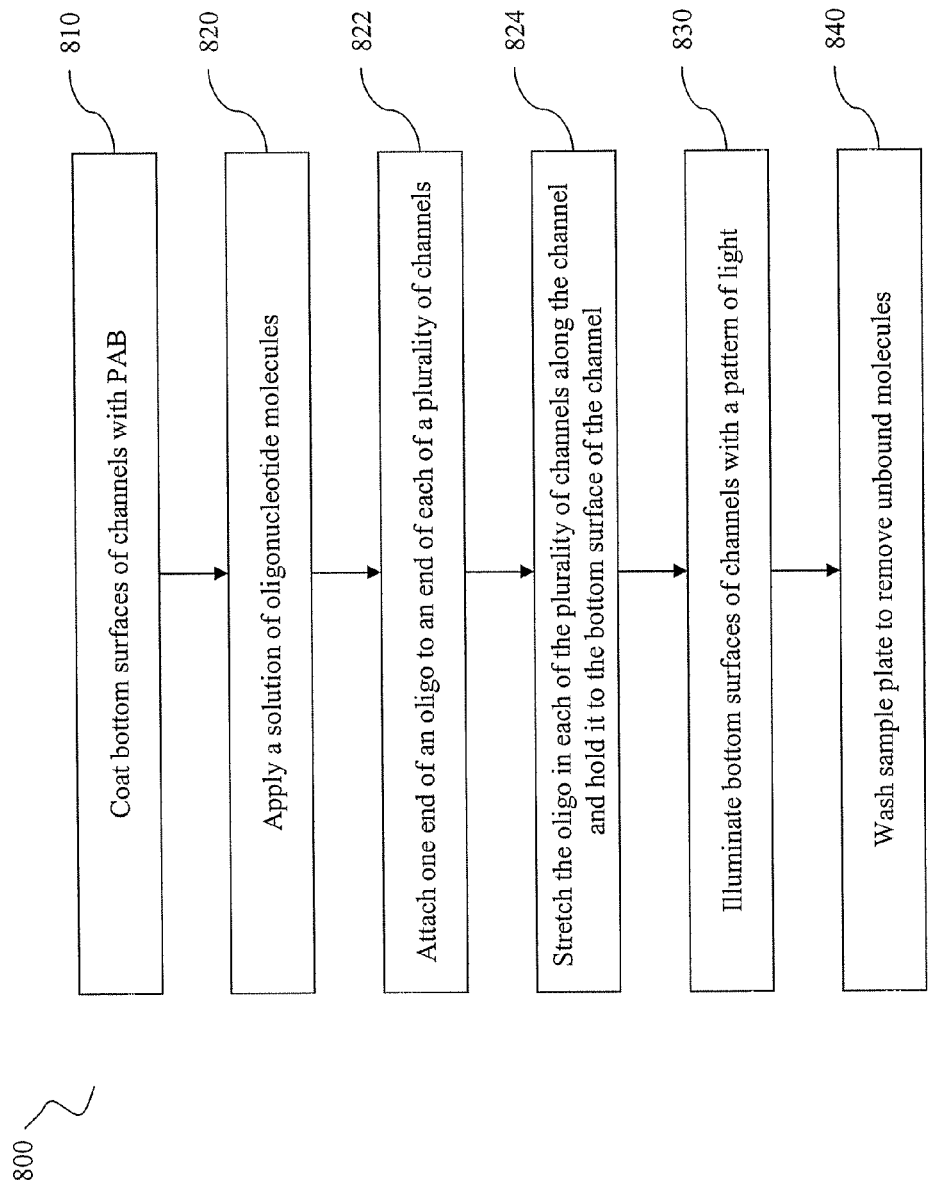
Figure 8C:
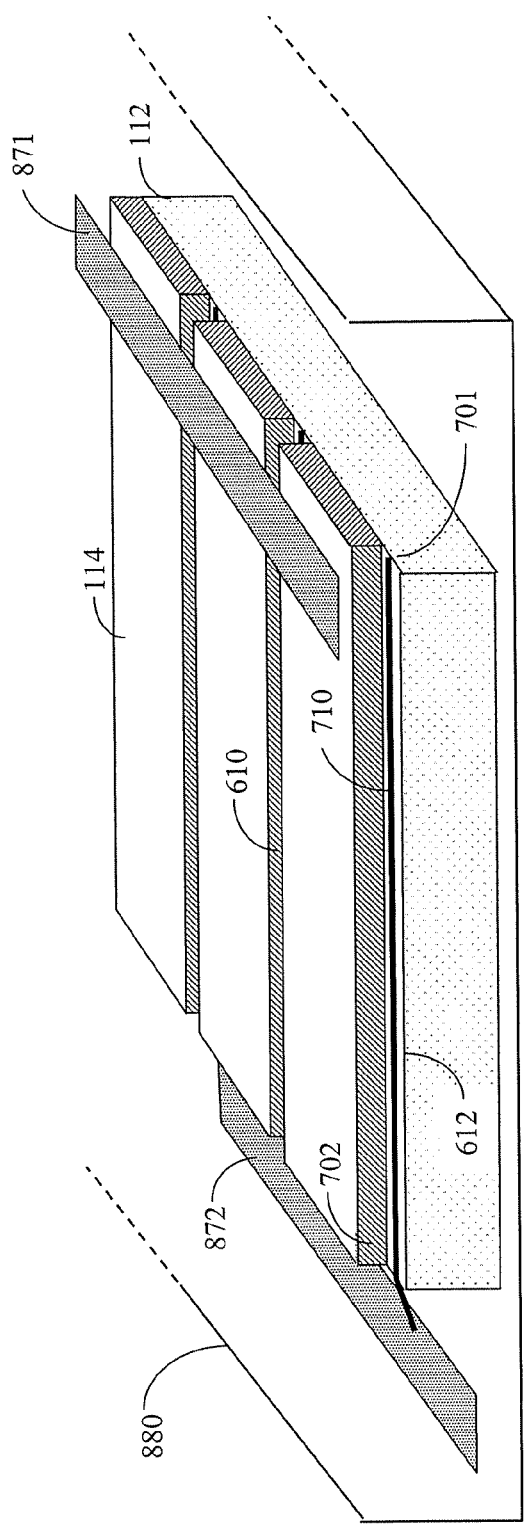
FIGS. 8C and 8D are diagrams illustrating embodiments of a setup for stretching each of a plurality of oligonucleotide molecules along a bottom surface of a channel on the sample holder.
Figure 8D:
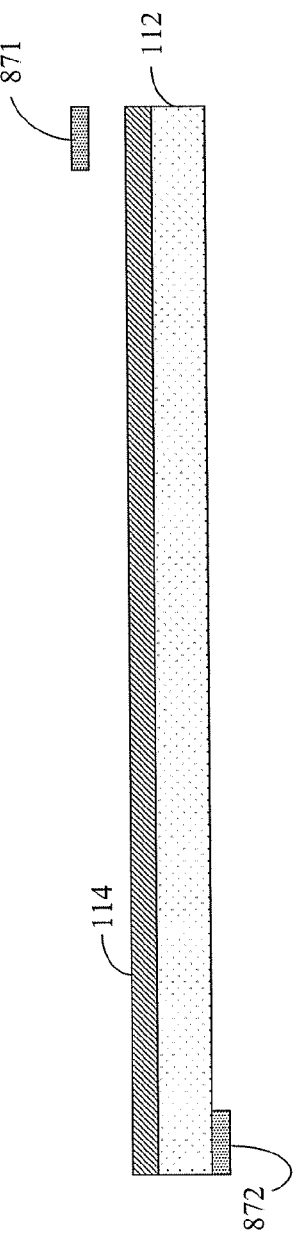

Referring to FIG. 8B, instead of enzyme or template molecules, a solution of oligonucleotide (oligo) molecules can be applied to the substrate in step 820, and additional steps can be used to stretch an oligo along the bottom surface of each of a plurality of channels 610 on the sample holder 110. As shown in FIG. 8B, to attach an oligo to the bottom surface of a channel 610, method 800 further comprises step 822 in which an end of the oligo is attached at one end 701 of the channel using a chemical linker, such as a biotin-streptavidin or PNA-PNA hybridization binding, where one part of the linker is attached to the end of the oligo and the other part of the linker is bound to the substrate. Method 800 further comprises step 824 in which the oligo is stretched along the channel and held to the bottom surface of the channel. Many conventional techniques of stretching DNA molecules can be used in step 824, including but not limited to hydrodynamic, electrostatic, and magnetic manipulations. For example, the oligo molecules can be stretched using dielectrophoresis, in which the oligo is stretched by a direct current (DC) electric field or a high-frequency (e.g., 1 MHz) and high-density (e.g., 1 MV/m) alternating-current (AC) field applied between two electrodes.

In one embodiment, as shown in FIG. 8C, the sample holder 110 can be placed in a container 880 for holding the fluid containing the oligonucleotides, an electrode 871 made of, for example, Indium Ti, is placed above the end 701 of the channel, and another electrode 872 made of the same or different conductive material as electrode 871 is placed in the container 880 below the bottom surface 612 of the channel 610 and near the other end 702 of the channel. A field is provided between the two electrodes 871 and 872 such that the oligo 710 is stretched along the channel 610 and held by the field along the bottom of the channel. Depending on the relative lengths of the oligo 710 and the channel 610, the oligo 710 may extend beyond the channel toward the electrode 872, if the channel is open at the end 702. Electrode 872 may also be placed under the substrate 112, as shown in FIG. 8C.

With the electric field still on, step 830 is performed to further attach the oligo 710 so that the field can be removed later, preventing the field from interfering with sequencing operation afterwards. The oligo in each of the plurality of channels may be stretched and attached simultaneously using the same or different electrodes.

After binding the enzyme, oligonucleotide, or target nucleic acid molecules to the sample holder 110, the sample holder 110 is placed in system 100. A fluorophore solution comprising fluorescence labeled nucleotide analogs is applied to the sample holder 110. In exemplary embodiments of the present teaching, the speed of chemistry of incorporation can be altered by changing the temperature, viscosity, and concentration of the fluorophore solution, and/or by modifying the base chemistry. For example, adding molecules such as dye molecules to the fluorophore solution has been found to slow the rate of base incorporation. In addition, the sample holder 110 in system 100 should ideally be under temperature control to insure consistency. The temperature could be changed during detection. For example, the temperature of the sample holder 110 can be reduced to slow down or stop incorporation activities until the rest of system 100 is ready to collect signals from the sample holder 110, as discussed below.

To observe light emitted from the source points, excitation light from light source 120 is directed towards the substrate side of the sample holder 110, and signals from fluorescing nucleotides are collected by optical assembly 130. The confinement of the source points on sample holder 110 helps to distinguish the fluorescent signals emitted by incorporated nucleotides in the source points 210 from those emitted by freely diffusing fluorescent ligands.

As explained in more detail below, multiple methods can be used in exemplary embodiments for base determination. For example, color, signal strength, bleaching life, fluorescent lifetime, and incorporation time can be combined to gain better base discrimination. The consistency of these measurements can be used to predict a confidence value for the base determination. Confidence values can be used to sort or weight the data and to discard data of low quality, thus allowing automated consensus generation from large amount of data. This can improve the quality of the consensus as well as providing a measure of confidence.

Prior art systems, such as the one described by Levene et al., 2003 in "Zero-Mode Waveguides for Single-Molecule Analysis at High Concentrations," SCIENCE, Vol. 299:682, which article is incorporated herein by reference, uses a confocal fluorescent set up. The confocal fluorescent set up has multiple shortcomings. First, the aluminum film reflects the excitation light directly back into the collection optics. The reflected excitation light is very intense compared to the fluorescent signals from incorporated nucleotides. To attenuate the reflected light, multiple filters are used, and each filter attenuates a significant percentage of the already weak fluorescent signals. Furthermore, the excitation light in the set up of Korlach and Levene, supra, can also excite fluorescence in the optics. This unwanted fluorescence could pass through the filters, increasing the background noise.

Figure 9:
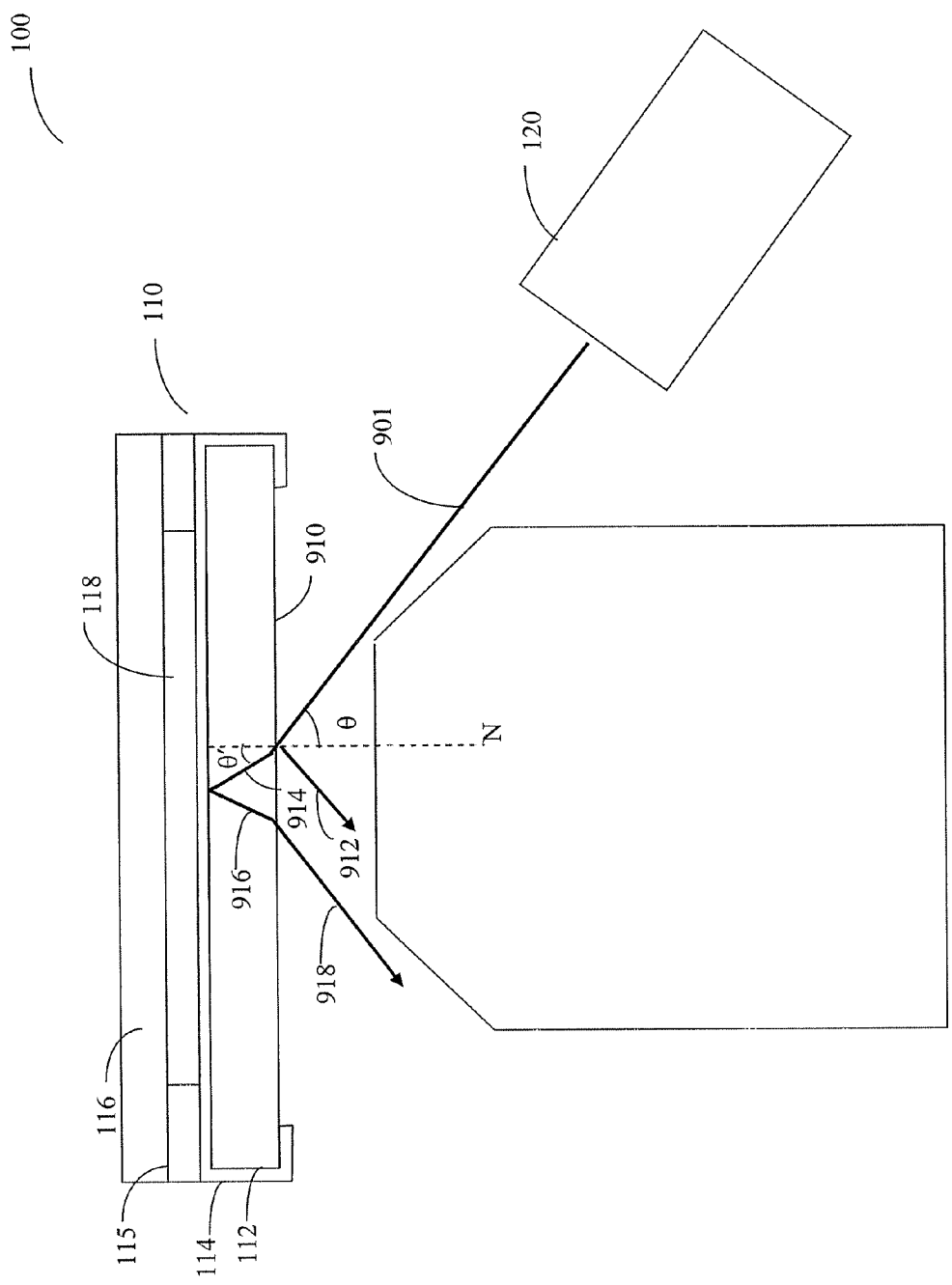
FIG. 9 is a block diagram illustrating exemplary embodiments of an optical arrangement useful for illuminating the source points placed on the sample holder.

In exemplary embodiments of the present teachings, excitation light from light source 120 is directed to the source points in sample holder 110 in an off-axis manner such that reflected excitation light, or a significant amount of it, could not enter the optical assembly 130. In some embodiments, where prism or wedge 108 is not provided, a light ray 901 from light source 120 is directed to sample holder 110 at an angle θ with respect to a normal direction N of substrate 112, as shown in FIG. 9. As the substrate 112 is made of a transparent material, such as fused silica, a relatively small first portion of the incident light 901 is reflected by the bottom surface 910 of substrate 112 and comes toward the optical assembly 103 as a first reflected light ray 912, while a second portion of the incident light enters the substrate at a different angle θ' with respect to the normal N as a refracted light ray 914. Angle θ' depends on angle θ and the refractive index n of the substrate 112. The refracted light ray 914 impinges on the metallic film at the angle θ' and a relatively large portion of the refracted light ray 914 is likely to be reflected by the metallic film 114 and comes toward the bottom surface 910 of substrate 112 as light ray 916. Light ray 916 when crossing the bottom surface 910 is refracted again and comes off the bottom surface 910 at the angle θ as light ray 918. With the off-axis arrangement and a proper selection of the angle θ, little of the light ray 918 should enter the optical assembly 130 placed under sample holder 110, as shown in FIG. 9.

To eliminate or reduce reflection at the bottom surface 910 of substrate 112, θ can be chosen to be within 10° of the Brewster's angle $θ_B$. Furthermore, to achieve zero or near zero reflection at the bottom surface 910 of substrate 112, the light from the light source 120 is linearly polarized with the E vector in the light parallel to the plane of incidence, which is the plane containing the incident ray 901 and the normal N of substrate 112. According to Brewster's Law, when the angle of incidence θ is equal to or near the Brewster's angle $θ_B$, the transmittance, i.e., the ratio of transmitted power in ray 914 to the incident power in ray 901 across bottom surface 910 of substrate 112 should be one or near to one and the reflected power in ray 912 from surface 910 should be zero or near zero. Brewster's angle $θ_B$ is given by:

$$θ_B = \tan^{-1}\left(\frac{n_2}{n_1}\right) = \tan^{-1}\sqrt{\frac{\varepsilon_2}{\varepsilon_1}}$$

where $n_1$ and $n_2$ are the refractive indices of the respective media, i.e., air and substrate 112, and $\varepsilon_1$ and $\varepsilon_2$ are their respective electric permittivity values.

Figure 10A:
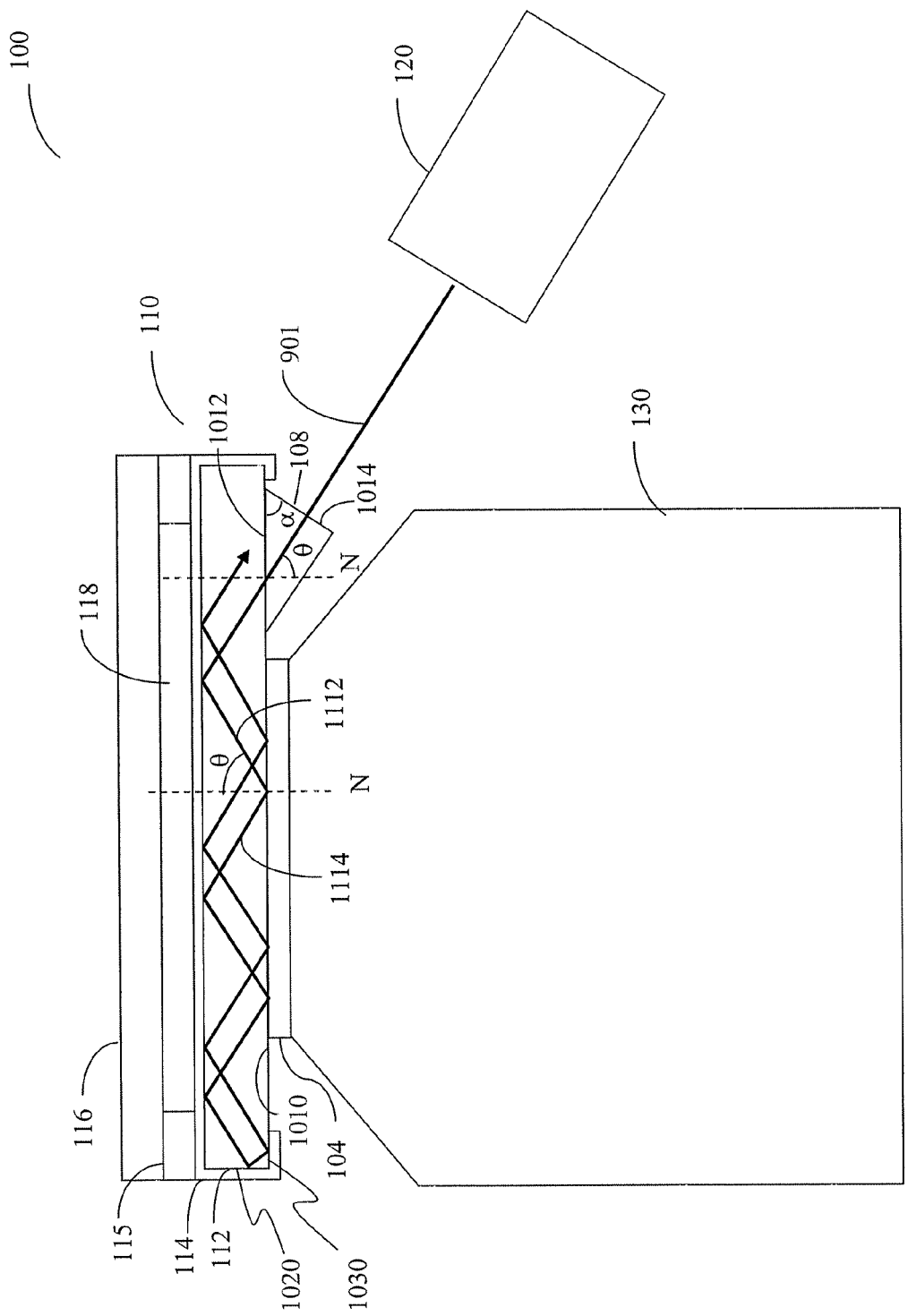
FIGS. 10A-10E are block diagrams illustrating further embodiments of an optical arrangement useful for illuminating the source points placed on the sample holder.
Figure 10B:
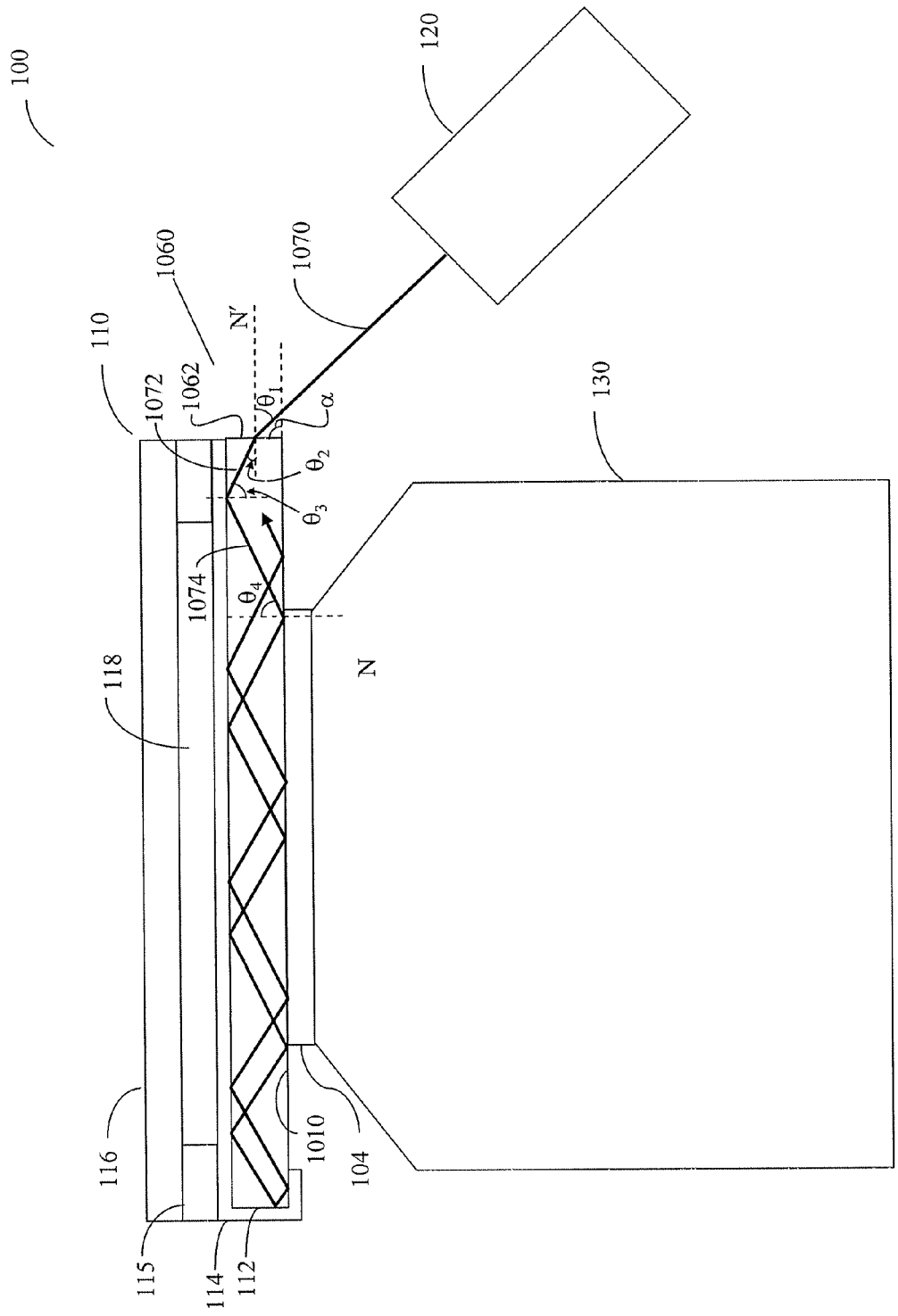
Figure 10C:
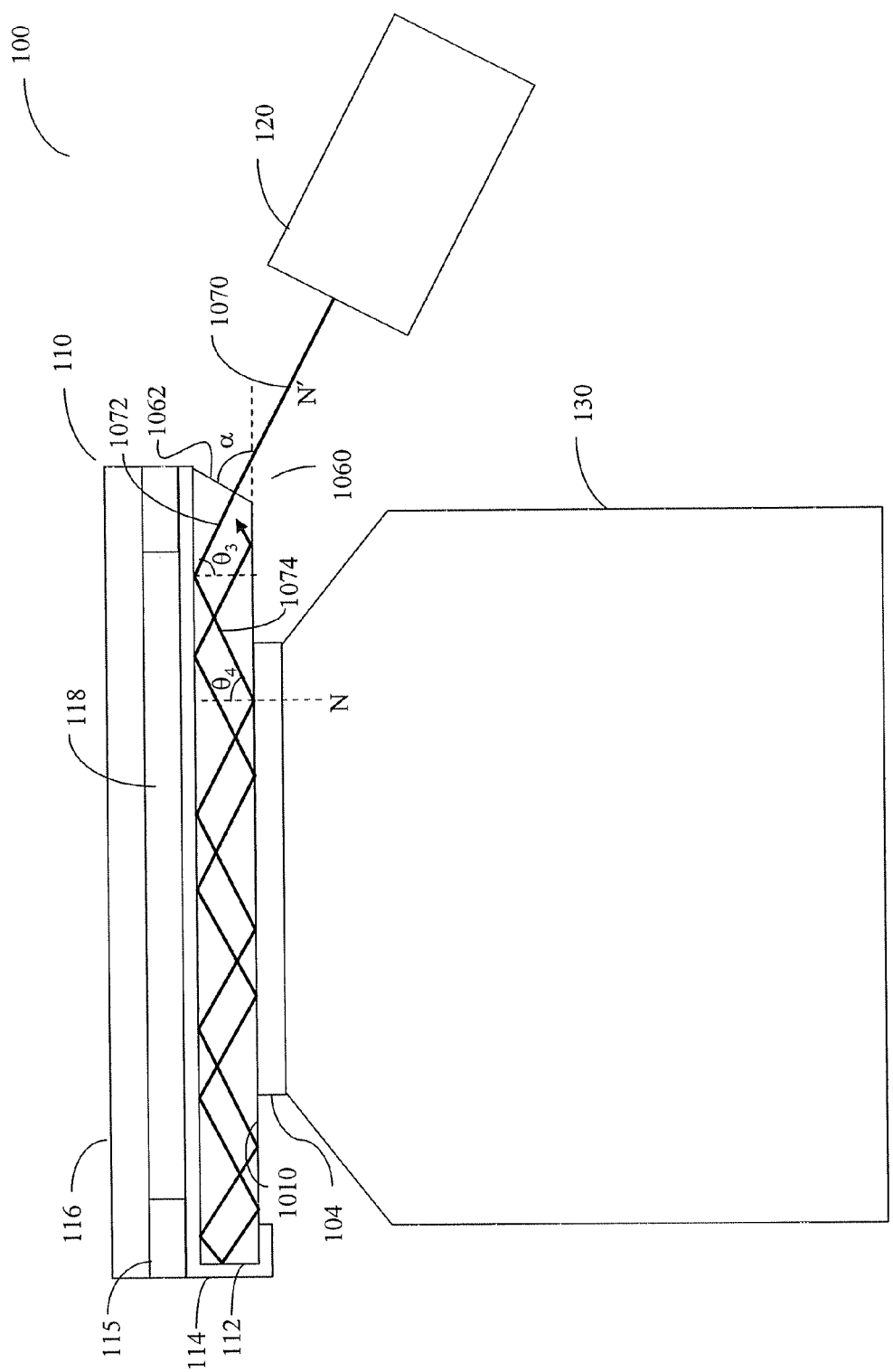

In some embodiments, system 100 is configured to achieve total internal reflection so that a significant amount of the excitation light from light source 120 is recycled within substrate 112, as shown in FIGS. 10A-10C. Total internal reflection is a phenomenon that light incident upon a boundary from a denser medium to a less dense medium is completely reflected off the boundary. Since the light ray 916 reflected from metallic film 114 has to travel through the substrate 112 toward the boundary 1010 between the substrate 112 and air, it is possible to achieve total reflection such that the light ray 916 is recycled in the substrate 112.

FIG. 10A illustrates an optical arrangement for achieving total internal reflection according to exemplary embodiments of the present teaching. As shown in FIG. 10A, prism 108 is ideally made of the same material as substrate 112 and is in direct or fluidic contact with the substrate. In exemplary embodiments, prism 108 is fused with substrate 112 at a first surface 1012 of the prism. Prism 108 has a second surface 1014 disposed at an angle α with respect to the first surface 1012. In some embodiments, angle α is selected to be equal to the incident angle θ of light ray 901 from light source 120. Thus, light ray 901 from light source 120 is directed toward the second surface 1012 of prism 108 along a normal direction of the second surface 1014 of the prism 108. While a small portion of light ray 901 may be reflected by surface 1014, the rest of light ray 901 enters substrate 112 without any change in direction because prism 108 and substrate 112 are ideally made of a same material and are fused together or optically coupled with each other with a fluid. A large portion of light ray 901 is reflected by metallic film 114 and comes off from the metallic film 114 as light ray 1112. Light ray 1112 impinges on the boundary 1010 between substrate 112 at angle equal to the angle θ with respect to the normal N of the substrate 112 from the inside of substrate 112.

In exemplary embodiments of the present teaching, θ is selected to be equal or larger than a critical angle $θ_τ$ such that light ray 1112 is totally reflected from boundary 1010 and comes back towards metallic film 114 as light ray 1114. The above reflection from the metallic film 114 and the total reflection at the boundary 1010 are repeated for light ray 1114 and its derivatives, which are the reflected portion of light ray 1114 and reflected portion thereof and so on, as shown in FIG. 10A. In exemplary embodiments, metallic film 114 is formed to extend to the side surfaces 1020 and in some embodiments to the edge portions 1030 of the bottom surface 910 of the substrate 112 so that light rays reflected from the metallic film 114 have little chance of escaping substrate 112 at the side surfaces 1020 but are recycled and used repeatedly as excitation light for the source points 210, as shown in FIG. 10A. According to Snell's Law, the critical angle $θ_τ$ is determined by:

$$θ_τ = \sin^{-1}\left(\frac{n_1}{n_2}\right),$$

where $n_1$ and $n_2$ are the refractive indices of the respective media, i.e., air and substrate 112, respectively.

In further embodiments, collection efficiency of optical assembly can be increased by using a fluid 104 having a refractive index between that of the air and that of the transparent material used to construct the substrate 112. For example, when substrate 112 is made of fused silica having a refractive index of about 1.46, water can be used as the fluid 104 because it has a refractive index of 1.33, which is between the refractive index of air (~1) and that of fused silica (~1.46). The fluid 104 is placed between the substrate 112 and the optical assembly 130. In the embodiments employing the fluid 104, the critical angle is determined by:

$$θ_τ = \sin^{-1}\left(\frac{n_f}{n_2}\right),$$

where $n_f$ is the refractive index of the fluid. The critical angle $θ_τ$ is therefore increased by employing the fluid. With the increase in the critical angle $θ_τ$, the collection efficiency is increased because more emitted light from the source points is able to escape through the bottom surface 910 of the substrate 112 without going through total internal reflection, and can therefore be collected by the optical assembly 130. The angle α of the prism 108 and the incident angle θ of the excitation light may be adjusted accordingly to allow total internal reflection of the excitation light to still occur in the presence of the fluid 104.

In another exemplary embodiment, as shown in FIG. 10B, total internal reflection is facilitated by directing the excitation light toward a side 1060 of the substrate 112. Excitation light 1070 from the light source 120 is directed to a side surface 1062 at an angle $θ_1$ with respect to a normal N' of the side surface 1062. A refracted portion 1072 of the excitation light 1070 leaves the side surface 1062 at an angle $θ_2$ that is dependent on the angle $θ_1$ according to the Snell's Law, and impinges on the aluminum film 114 on top of the substrate 112 at an angle $θ_3 = α - θ_2$, where α is the angle between the side surface 1062 and the bottom surface 1010 of the substrate 112. After reflection from the aluminum film, a reflected portion 1074 of the excitation light impinges on the surface 1010 at an angle $θ_4$ that is equal to the angle $θ_3$. $θ_2$ and α can be selected such that $θ_3$ or $θ_4$ is equal to or larger than the critical angle $\theta_r$ for total reflection at the bottom surface 1010 of the substrate 112. For example, α in this case can be selected to be at or near 90° in order to create a large $\theta_3$ or $\theta_4$ angle. Thus, most of the refracted portion 1072 of the excitation light 1070 can be repeated used to illuminate the source points on the sample holder 110 before exiting the substrate 112.

In another exemplary embodiment, as shown in FIG. 10C, the side 1060 has a beveled surface 1062 forming an angle α with the bottom surface 910 of the substrate 112, where α is less than 90° and larger or equal to the critical angle $\theta_r$. Excitation light 1070 from the light source 120 is directed to the beveled surface 1062 along a normal N' of the beveled surface 1062. A refracted portion 1072 of the excitation light 1070 leaves the beveled surface 1062 at an angle $\theta_2$ that is dependent on the angle $\theta_1$ according to the Snell's Law, and impinges on the aluminum film 114 on top of the substrate 112 at an angle $\theta_3 = \alpha$. After reflection from the aluminum film, a reflected portion 1074 of the excitation light impinges on the surface 1010 at an angle $\theta_4$ that is equal to the angle $\theta_3$. With α being equal or larger than the critical angle $\theta_r$, $\theta_4$ is also equal or larger than $\theta_r$ and total reflection occurs at the bottom surface 1010 of the substrate 112.

Figure 10D:
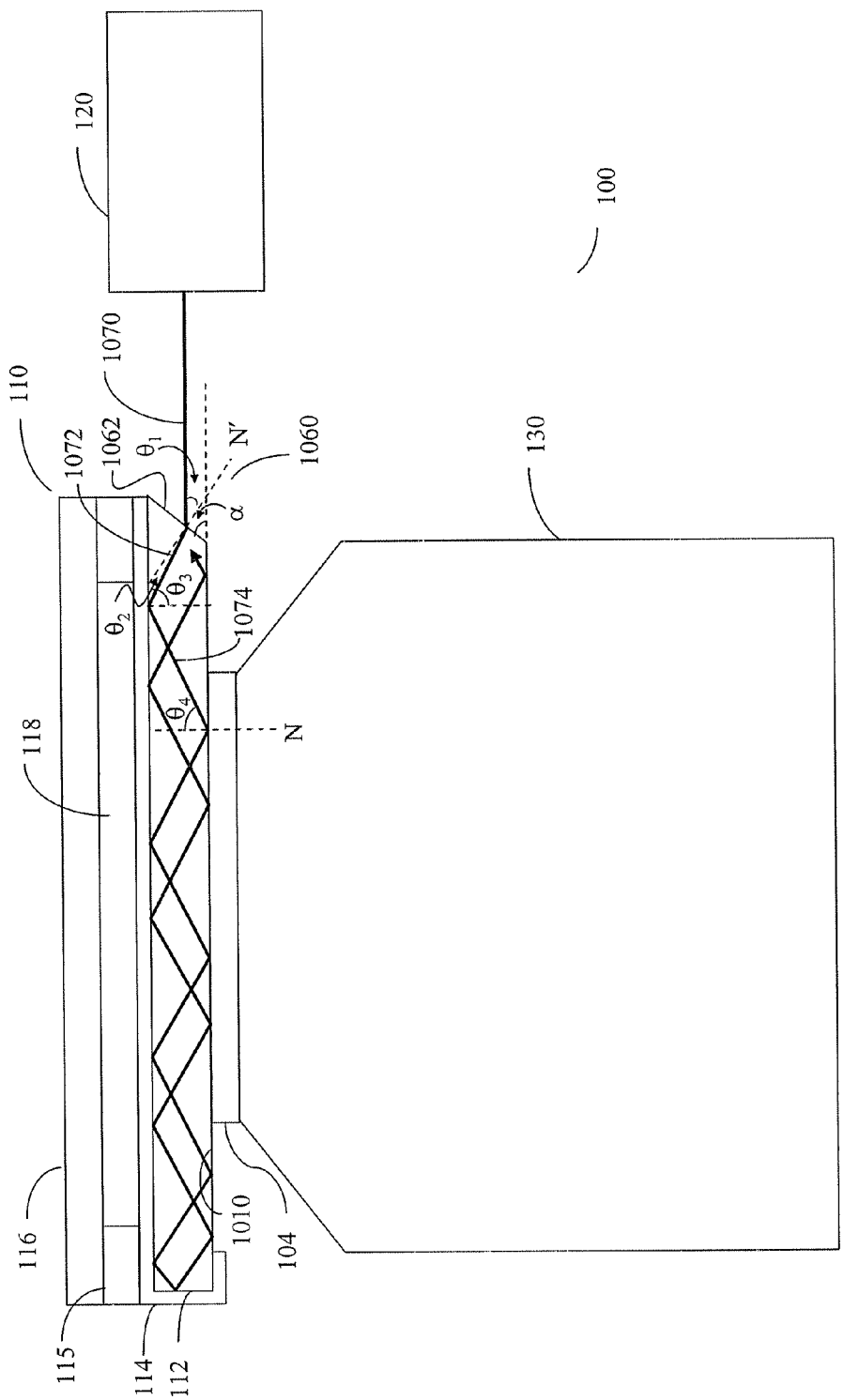

In another exemplary embodiment, as shown in FIG. 10D, the side 1060 has a beveled surface 1062 forming an angle α with the bottom surface 910 of the substrate 112, and excitation light 1070 from the light source 120 is directed to the beveled surface 1062 at an angle $\theta_1$ with respect to a normal N' of the beveled surface 1062. A refracted portion 1072 of the excitation light 1070 leaves the beveled surface 1062 at an angle $\theta_2$ that is dependent on the angle $\theta_1$ according to the Snell's Law, and impinges on the aluminum film 114 on top of the substrate 112 at an angle $\theta_3 = \theta_2 + \alpha$. After reflection from the aluminum film, a reflected portion 1074 of the excitation light impinges on the surface 1010 at an angle $\theta_4$ that is equal to the angle $\theta_3$. $\theta_2$ and α can be selected such that $\theta_3$ or $\theta_4$ is equal to or larger than the critical angle $\theta_r$ for total reflection at the bottom surface 1010 of the substrate 112. Thus, most of the refracted portion 1072 of the excitation light 1070 can be repeated used to illuminate the source points on the sample holder 110 before exiting the substrate 112.

Figure 10E:
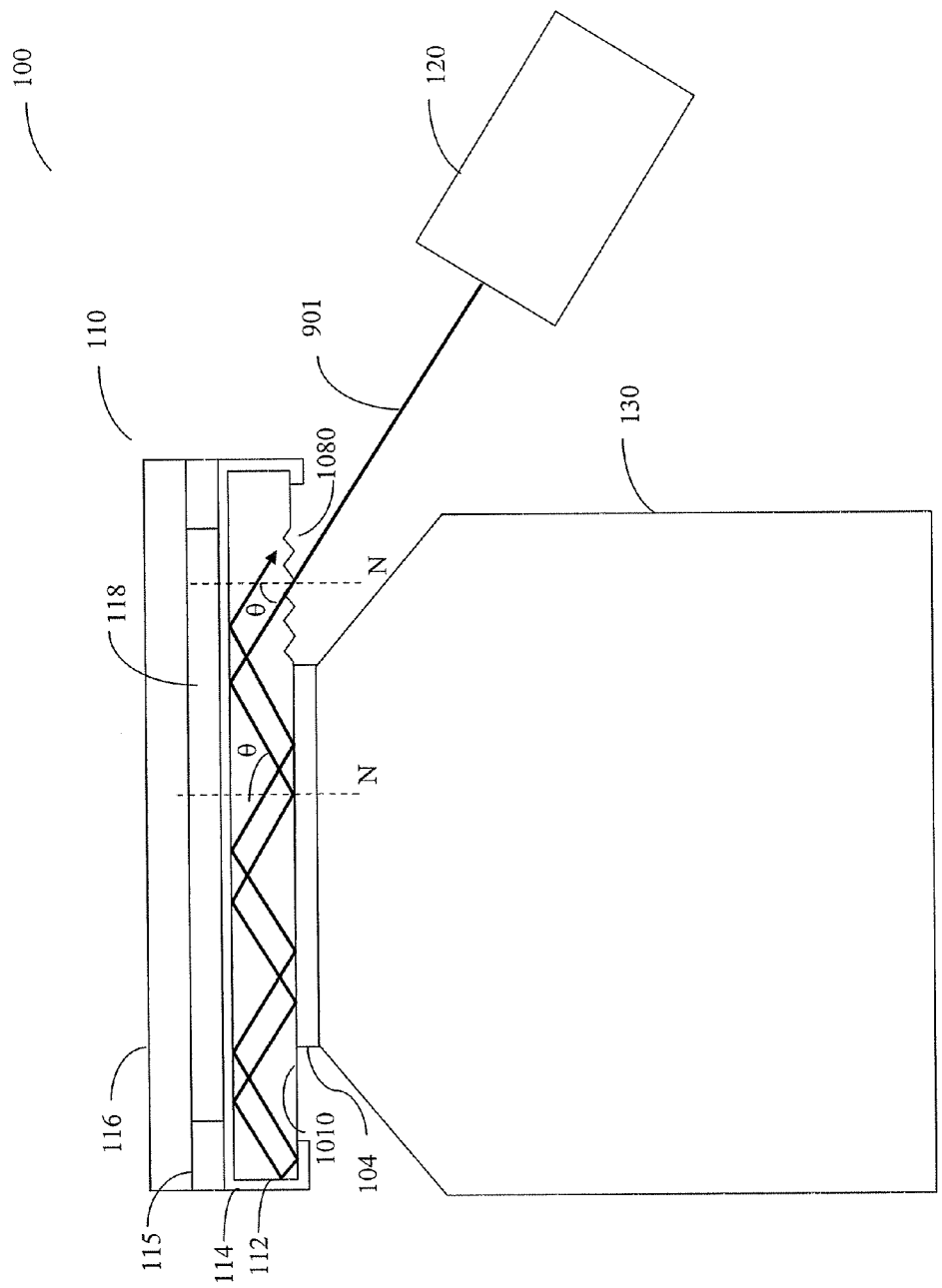

In another exemplary embodiment, the excitation light 901 from the light source 120 is coupled into the substrate 112 through a grism, which is a prism and grating combination, or grating 1080 formed on or attached to a portion of the bottom surface 1010 of the substrate 112, as shown in FIG. 10E. With the use of the grism or grating 1080, the excitation light 901 can enter the substrate at an angle θ with respect to the normal N of the substrate that is equal or larger than the critical angle $\theta_r$, and after being reflected from the aluminum film 114, would impinge on the bottom surface 1010 of the substrate 112 at the angle θ and be totally reflected from the bottom surface 1010 back into the substrate. Thus, the excitation light is recycled within the substrate, as shown in FIG. 10C.

The arrangements in FIGS. 9 through 10E are advantageous over conventional systems in part because, by placing the detector(s) and the optical assembly 130 under sample holder 110, fluorescent signals can be collected through the bottom surface 910 of the sample holder 110 without the interference of reflected light from metallic film 114. Furthermore, since the excitation light and the fluorescent signals entering the optical assembly 130 do not have a common light path, there is no need of heavy filtering to separate the excitation light entering the substrate 112 from the fluorescent signals exiting the substrate 112 through the bottom surface 910.

Figures 11, 12:
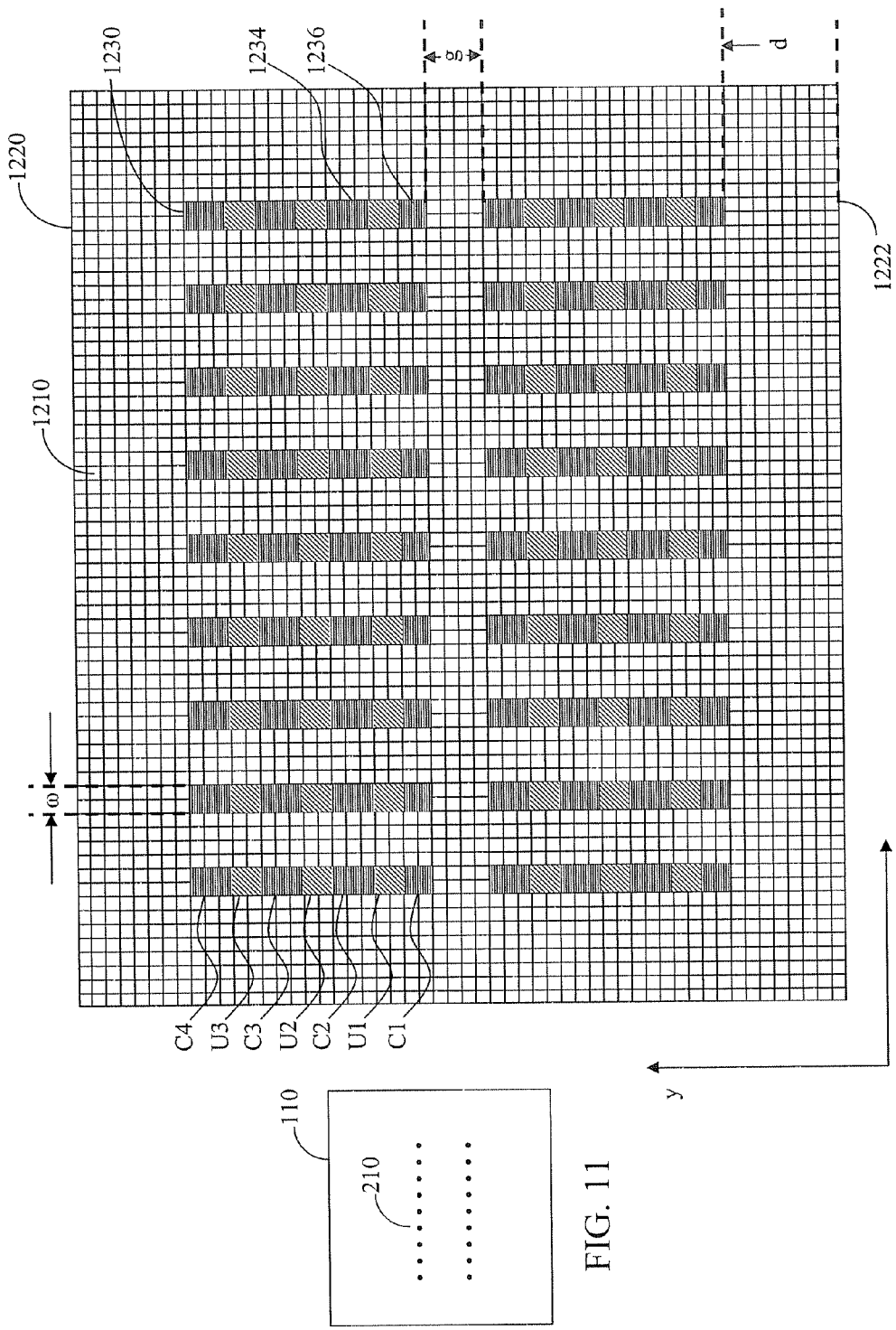
FIG. 11 is top view of a sample holder showing a plurality of source points.
FIG. 12 is a top view of an image plane in a detector in the system in FIG. 1 according to exemplary embodiments.

In various embodiments, optical assembly 130 comprises at least one pixilated or multi-element detector configured to sense light signals landed thereon and a set of optical components configured to direct light emissions from the source points toward the multi-element detector(s). FIG. 11 illustrates a top view of a portion of the sample holder 110 showing a plurality of source points 210. In exemplary embodiments, as shown in FIG. 12, the pixilated or multi-element detector comprises a plurality of addressable light-sensing elements 1210 organized in an imaging plane 1220, such as the x-y plane. The set of optical components is configured to direct light emissions from different source points toward different areas 1230 of the imaging plane 1220 so that light emissions from different source points 210 can be separately and substantially simultaneously detected.

Thus, as shown in FIG. 12, light emissions from each source point 210 form an image of the source point in an area 1230 on the imaging plane 1220. In exemplary embodiments, the set of optical components further comprises a light-dispersing setup configured to separate light emissions from the multiple source points 210 into multiple spectral components so that the detected light from each source point is spread out spectrally along the y axis and images 1230 represent spectrally resolved images of the source points 210, as shown in FIG. 12. When the light-dispersing setup is provided, enough separation between neighboring source points 210 on the sample holder 110 is provided to insure that the spectrally resolved images 1230 of the source points do not overlap with each other. In addition, sufficient gap g along the y-direction between an image 1230 of a source point and an image 1230 of a neighbor source point are provided to prevent overlap of data associated with the two source points due to cutoff filter tolerances.

The position of the images 1230 can be determined by a spatial calibration to associate each source point on the sample holder with an area 1230 on the image plane 1220. The calibration can be done by using a dye solution or a light source that is not blocked by system filters. Such calibration, however, may not be required if there is no need to correspond the images 1230 with the source points 210. In addition, tolerance should be allowed to insure that there is sufficient separation d between the areas 1230 and the edges of the image plane 1220, and the separation should be controlled to allow detection of all of the source points 210 on the image plane 1220. As a non-limiting example, the buffer zone d between a side 1232 of an areas 1230 facing an edge 1222 of the image plane 1220 is no more than 8 pixels wide.

Although FIG. 12 shows that the source point images 1230 each having a width ω of 2 pixels, a pitch between two neighboring images in the x-direction being 4 pixels, a gap g between two adjacent rows of images being 4 pixels, and a buffer distance d of the images 1230 from each edge of the image plane 1220 being 8 pixels, these numbers are shown as examples and can be different in different applications or are adjustable to suit different applications. Moreover, although FIG. 12 shows only two rows of source points 210 and two rows of images 1230 corresponding to the source points, in practice, there may be more or less rows of source points or images. Also, the source points 210 do not have to be arranged in rows and can be spread out on the sample holder in any order or even randomly as long as they are sufficiently separated so that their images 1230 do not overlap on the image plane 1220.

Figure 13:
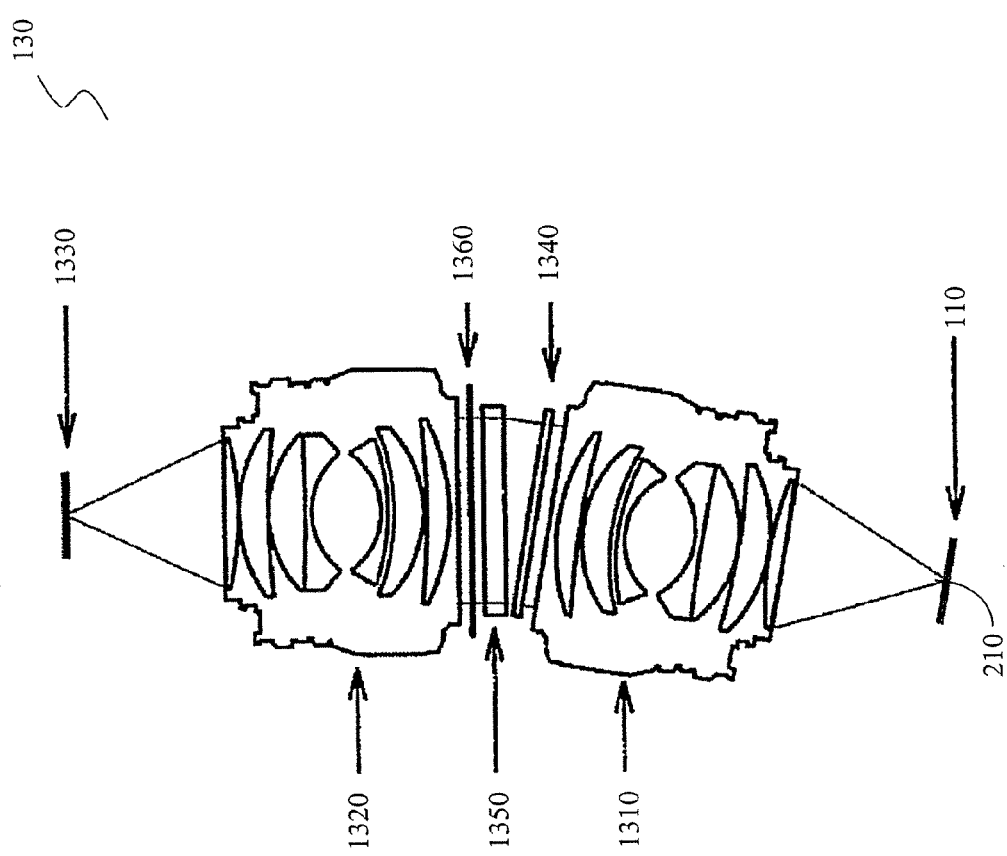
FIG. 13 is a diagram illustrating an optical assembly for detecting light signals from the source points on the sample holder according to exemplary embodiments.

In exemplary embodiments, the optical assembly 130 is similar to the one in the optical system disclosed in U.S. Pat. No. 6,690,467 B1 by Reel, which is incorporated herein by reference. As shown in FIG. 13, as a non-limiting example, the optical assembly comprises a collection lens assembly 1310, a reimaging lens assembly 1320, and at least one CCD detector 1330 as the pixilated detector. The collection lens assembly 1310 comprises at least one collection lens configured to collect light emissions from the source points 210. The reimaging assembly 1320 comprises at least one reimaging lens configured to focus the collected light emissions from different source points into different areas 1230 of the imaging plane 1220 of the detector 1330.

The use of the collection lens assembly 1310 may also provides a substantially collimated region between the collection lens assembly 1310 and the reimaging lens assembly 1320, which is suitable for insertion of a variety of optical devices such as a an aperture 1340, a light-dispersing assembly 1350, and/or a laser line filter 1360. In exemplary embodiments, the light-dispersing assembly 1350 comprises at least one grating, prism, or grism configured to spread spectrally rays of light that pass through it. For example, a transmission grating deflects rays of light that strike thereon at an angle roughly proportional to the wavelength of the light. Thus, the collimated light emissions from the source points 210, after going through the transmission gratings, are dispersed spectrally. With the spectral dispersion, a first light ray of a first wavelength and a second light ray of a second wavelength coming from a same source point 210 should arrive at the reimaging lens assembly 1320 at different angles with respect to an optical axis of the reimaging lens assembly 1320 and thus be focused onto different locations 1234 and 1236 of the area 1230 corresponding to the source point, as shown in FIG. 12. Locations 1234 and 1236 are spaced apart from each other along the y-axis because of the spectral dispersion.

Figure 14A:
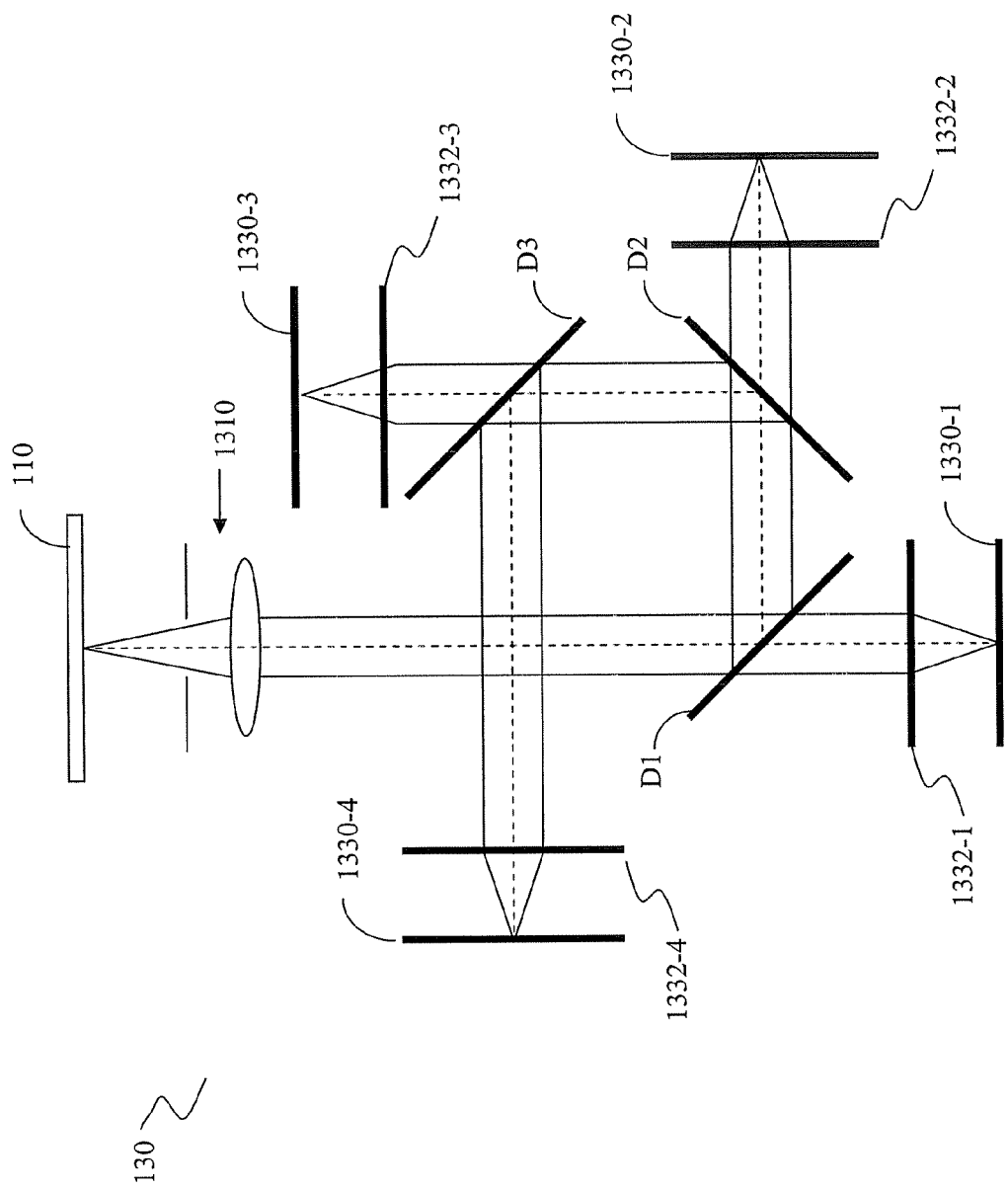
FIGS. 14A-14C are diagrams illustrating further embodiments of an optical assembly for detecting light signals from the source points on the sample holder.

Instead of prism, grating, or grism in the light dispersing assembly 1350, dichoic or bandpass filters can be used to separate the spectral components in the fluorescent signals from each source point. FIG. 14A illustrates other embodiments of optical assembly 130. As shown in FIG. 14A, optical assembly 130 comprises a collection assembly 1310, an imaging assembly comprising imaging lenses 1332-1, 1332-2, 1332-3, and 1332-4 disposed at 90° angles with respect to each other, a plurality of CCD detectors 1330, and a light dispersing assembly comprising dichroic or bandpass filters D1, D2, and D3 placed at 90° angles with respect to each other. Each dichroic or bandpass filter is configured to allow passage of one of the first, second, and third bands of fluorescent signals, respectively, and to reflect all other frequencies. The plurality of CCD detectors 1330 comprises CCD detectors 1330-1, 1330-2, 1330-3, and 1330-4. CCD detector 1330-1 is placed behind dichroic filter D1 to collect the first band of fluorescent signals, CCD detector 1330-2 is placed behind dichroic filter D2 to collect the second band of fluorescent signals, CCD detector 1330-3 is placed behind dichroic filter D3 to collect the third band of fluorescent signals, and CCD detector 1330-4 is placed in front of dichroic filter D3 to collect the signals reflected therefrom, which should comprise the fourth band of fluorescent signals. Other filters (not shown) can be placed before CCD detectors 1330, respectively, for improved frequency selection.

Figure 14C:
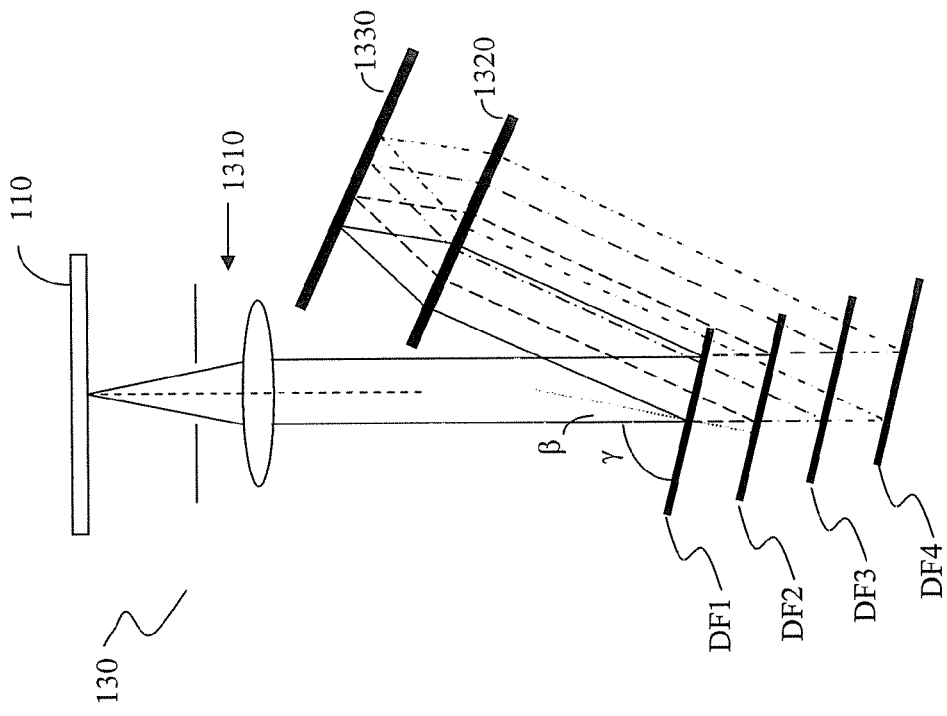
Figure 14B:
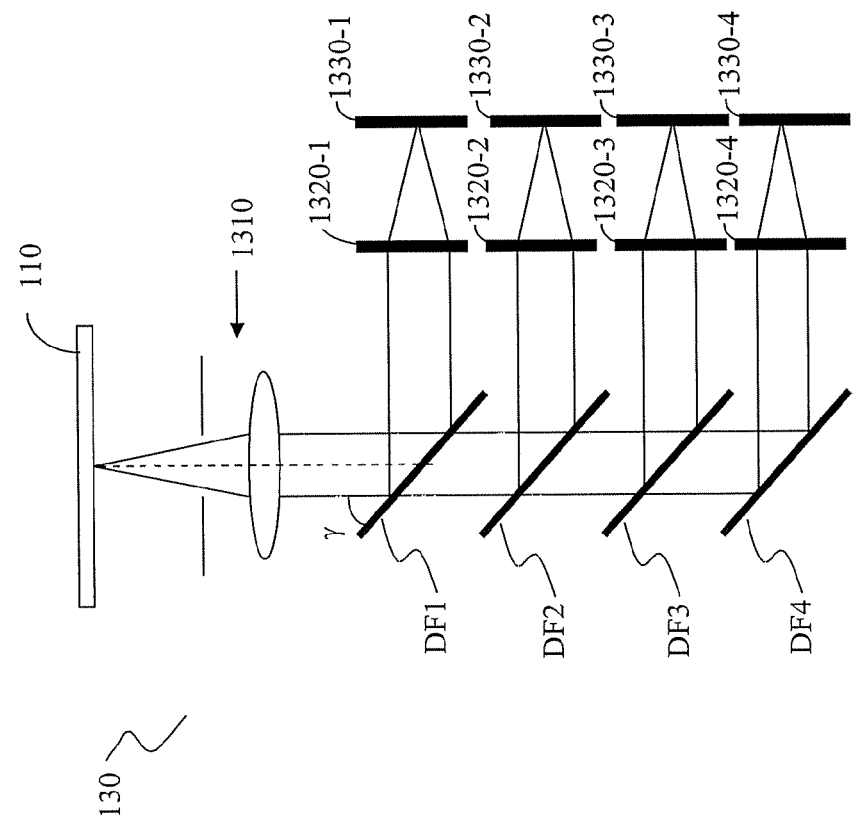

Alternatively, a dichroic or bandpass filter can be configured to reflect the first, second, third, or fourth band of fluorescent signals, and to allow passage of all other frequencies. It is also possible to combine bandpass, notch, lowpass and highpass filters in any combination that permits appropriate separation of the emission wavelengths. FIG. 14B illustrates still other embodiments of optical assembly 130. As shown in FIG. 14B, optical assembly 130 comprises a collection lens assembly 1310, a reimaging assembly comprising reimaging lenses 1320-1, 1320-2, 1320-3 and 1320-4, and CCD detectors 1330-1, 1330-2, 1330-3, and 1330-4 each behind a respective one of the reimaging lenses 1320-1, 1320-2, 1320-3 and 1320-4. Optical assembly 130 further comprises a light dispersing assembly comprising dichroic or bandpass filters DF1, DF2, DF3 and DF4 placed in a row under collection assembly 1310 and each at an angle γ to an optical axis (shown by the dashed line) of the collection assembly 1310. Dichroic or bandpass filters DF1, DF2, DF3, and DF4 are each placed in front of a respective one of the reimaging lenses 1320-1, 1320-2, 1320-3 and 1320-4 and are configured to reflect the first, second, third and fourth bands of fluorescent signals, respectively, while allowing passage of signals of other frequencies. Other filters (not shown) can be placed before CCD detectors 1330, respectively, for improved frequency selection.

Imaging lenses 1320-1, 1320-2, 1320-3 and 1320-4 can be separate lenses or sections of a single lens, CCD detectors 1330-1, 1330-2, 1330-3, and 1330-4 in FIG. 14B can be separate CCD detectors or sections of a single CCD detector. Although FIG. 14B shows that the dichroic or bandpass filters DF1, DF2, DF3 and DF4 are at a roughly 45° angle with respect to the optical axis of the collection assembly 1310, such placement is not necessary and the angle γ can be larger or smaller than 45°. FIG. 14C illustrates an exemplary configuration of the optical assembly 130 when the angle γ is close to 90° so that the collimated light emissions from a source point would impinge on the dichroic or bandpass filters DF1, DF2, DF3 and DF4 at a small incident angle β and be imaged by the reimaging lens assembly 1320 onto the CCD detector(s) 1330.

The CCD assembly 1330 comprises at least one charge-coupled device (CCD) array, such as a regular CCD array, a complimentary metal-oxide-semiconductor (CMOS) array, an electron-multiplying CCD (EMCCD) array, an intensified CCD (ICCD) array, or an electron-bombarded CCD (EB-CCD) array. A CCD array is advantageous over other multi-element detectors, such as an array of avalanche photodiode (APD) based detectors or photomultiplier tube (PMT) based detectors, because the number of elements in a CCD array is much higher, as the size of a CCD pixel in the CCD array can be as small as 3 μm or even smaller. Therefore, signals from different source points can be differentiated by detecting them using different groups of elements in the CCD array, as discussed above. A CCD array can be much less costly than an APD or PMT array.

To amplify the low light signals from fluorescing labels on the incorporated bases above background noises in CCD arrays, a high-sensitivity CCD-based device such as EMCCD, ICCD, or EB-CCD, is used in exemplary embodiments. Due to fast base incorporation rates of DNA molecules, in addition to sensitivity, the speed of reading data out from a CCD detector is also important because it is associated with the ability to capture event data and to readout the data out over a short period of time to allow the next event to be observed. Through careful design of a readout scheme, a CCD array can be made to be fast enough to resolve fluorescent emissions from two consecutive incorporation events associated with a same source point. Moreover, a CCD with multiple outputs or taps can be used to increase the CCD readout speed. For example, a CCD with 4 taps can allow a 4-times increase in readout speed, which allows images of more source points to be read for increased throughput.

To further improve the readout speed, a frame transfer CCD (FTCCD) array 1500, as illustrated in FIG. 15A, is used in detector 1330 according to exemplary embodiments of the present teaching. The FTCCD array 1500 allows data readout operations to be performed concurrently with data collection operations. As shown in FIG. 15A, CCD array 1500 comprises a dark area 1510, an image area 1520, a masked storage area 1530, and a horizontal register 1540. The image area 1520 of CCD array 1500 is where light signals are detected and is constructed as a two-dimensional array of light-sensitive elements or pixels. Storage area 1530 comprises an array of storage elements covered with an opaque mask to provide temporary storage for an image frame transferred from the image area. The signal that is accumulated in each pixel in image area 1520 is read out by a process of parallel transfer in the negative y-direction shown in the figure, whereby charges in each horizontal row within image area 1520 and storage area 1530 are transferred to the next row and so forth until ultimately they reach the horizontal register 1540, which is a serial readout register that allows charges to be transferred in the x-direction to an output node (not shown), from which they are read out. While data from storage array 1530 is read, image area 1520 is available to collect a next round of light signals.

Dark area 1510 is a region of excess pixels. Because these pixels are not illuminated, they do not have to be cleared during each readout. Usually, the combination of dark area 1510 and image areas 1520 maps directly onto the storage area 1530. In one embodiment, image area 1520 occupies a small fraction (e.g. 1/10) of the combination so that source point data can be read out at, for example, 10 times the normal frame rate. In exemplary embodiments, CCD array 1500 is kept cool at about 80° C. below zero so that minimal dark current charges are generated. In certain embodiments, the dark area is eliminated when CCD 1500 is custom built to have just the right amount of rows in the image area 1520.

In some embodiments, an interline CCD or a combined interline and frame transfer CCD may be employed. FIG. 15B illustrates an interline CCD array 1550 in CCD detector 1330 according to exemplary embodiments of the present teaching. As shown in FIG. 15B, interline CCD array 1550 comprises separate image regions 1560 and CCD storage regions 1570. CCD storage regions 1570 are protected with a mask structure and positioned alongside respective ones of image regions 1560 such that CCD storage regions 1570 and image regions 1560 together form an alternating parallel array. Image regions 1560 may comprise circuit elements such as photodiodes for capturing the images of the source points while CCD storage regions 1570 shift previously acquired images in a parallel fashion towards a horizontal register 1590. The horizontal register 1590 then sequentially shifts image information from each CCD storage region to an output amplifier or other processing circuits (not shown) as a serial data stream. The readout process is repeated until data from all of the CCD storage regions 1570 are transferred to the output amplifier.

Where an actual two-dimensional image is desired from the CCD, the image data in a digital format is reconstructed to yield the final image. Where the data is to be used for non-pictorial or non-imaging applications, the relevant pixel data may be identified and processed according to its intended purpose. One advantage of the interline CCDs is their ability to operate without a shutter or synchronized strobe, allowing for an increase in device speed and faster frame rates. An interline CCD array can be used to eliminate blurring or image smear, which is a common problem with frame-transfer CCDs, by effectively doing horizontal shifts directly from the image regions to the respective ones of the storage regions.

In exemplary embodiments, readout speed is further improved by limiting the number of source points to be imaged on the CCD so that the number of data rows to be read are minimized. The number of data rows to be read may also be minimized by binning vertically (in the y-direction), especially when the source points 210 and thus the images of the source points 1230 are in an array so that the positions of the images can be fairly accurately predicted, as shown in FIG. 12. With the fluorescent signals dispersed spectrally over a range of pixels along the y-direction, the pixels can be binned in the y-direction to capture informative wavelength groupings for base determination. For example, as shown in FIG. 12, each source point image 1230 may comprise four interested wavelength groups C1, C2, C3, and C4 interleaved with uninterested wavelength groups U1, U2, and U3. Data in each of the interested wavelength groups can be binned, while data in the uninterested wavelength groups can be cleared without being read, as discussed below. Binning can also be done in the x-direction for further increase in readout speed because shifting is often faster than reading. With a CCD array, binning can be done on-chip in a conventional manner that does not introduce noise.

The CCD array in detector 1330 may also be made to allow clearing of the horizontal register 1540 or 1590. This can speed up readouts if desired data is separated by rows of unneeded pixels. FIG. 16A illustrates examples of four normalized fluorescent spectra associated with the four different fluorescent labels used to label respective ones of four different nucleotides. The four spectra have peak regions 1610, 1620, 1630, and 1640 corresponding to respective ones of the first, second, third and fourth frequency bands. Only four fluorescent frequency bands need to be collected by detector 1330. Data can be over-determined, however, to comprise more than the spectrum of data associated with an incorporation event. With the light dispersing setup shown in FIG. 13, a continuous portion of a spectrum of data is spread along the y-direction, as shown in FIG. 16B. FIG. 16C illustrates the over-determined data with the most informative wavelengths corresponding to the four frequency bands in gray and the less informative wavelength ranges shown in white. Data rows in the less informative wavelength range between two gray bands is referred to as a band gap bg, which may not be needed and can be cleared without being read out for increased readout speed. The width and position of each informative frequency band in FIG. 16C can be optimized for best signal to noise (S/N) ratio after multicomponenting, as explained in more detail below.

While the frequency bands in FIGS. 12, 16B, and 16C are shown to spread along the y-direction, this is not essential and orienting the frequency bands in a different direction on the CCD may be advantageous in some cases.

Figure 17A:
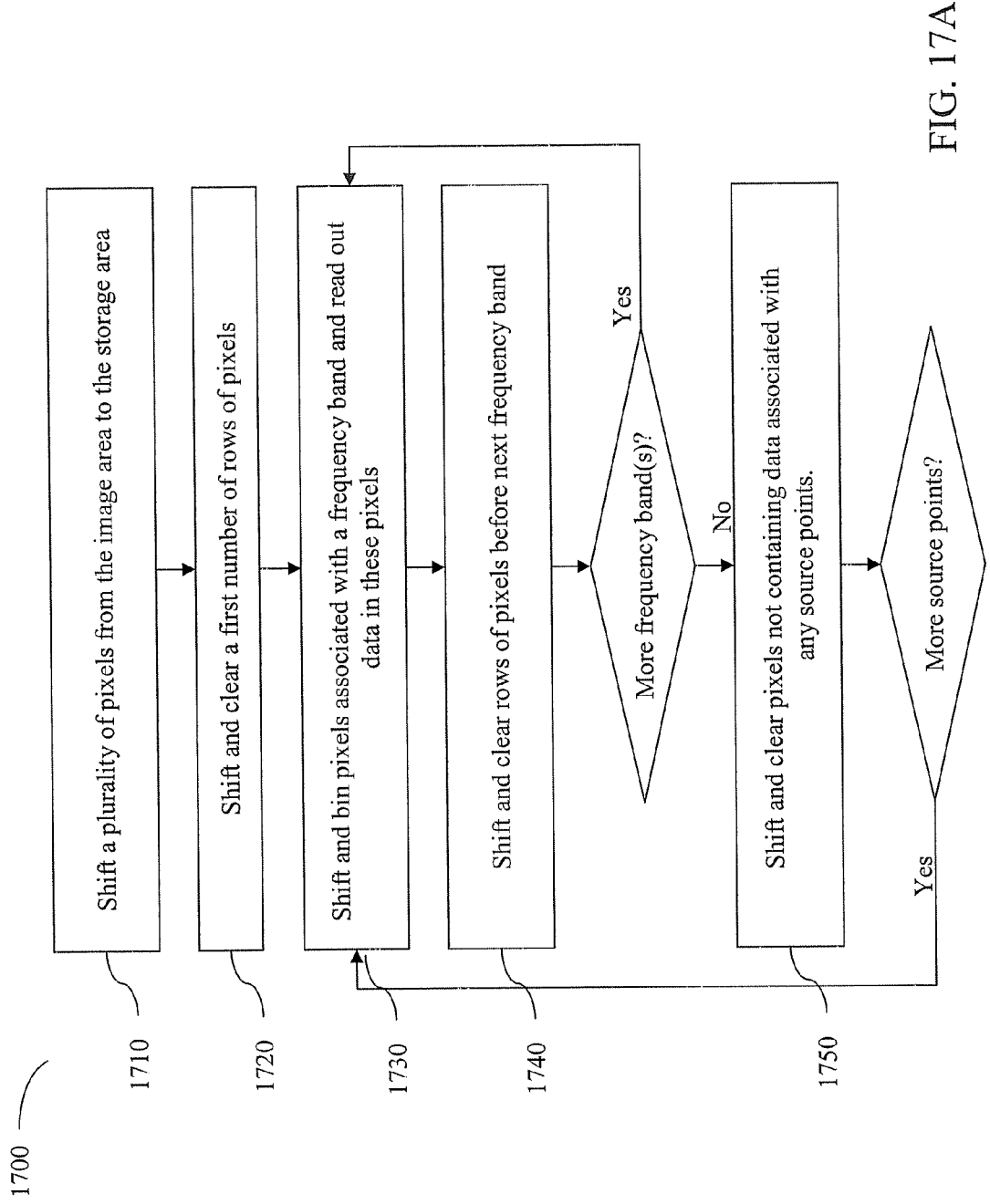
FIG. 17A is a flowchart illustrating a method for reading out CCD data associated with a plurality of source points according to exemplary embodiments.

FIG. 17A is a flow chart of a method 1700 for reading out image data associated with a plurality of source points according to exemplary embodiments of the present teaching. As a non-limiting example, method 1700 is described in the context of a frame transfer EMCCD array of 512×512 pixels in the image area that allows clearing of the horizontal register. Nevertheless, the method can be readily adapted to other types of CCD array. As shown in FIG. 17A, method 1700 comprises step 1710 in which the pixels in the image area are shifted down by a frame having, for example, 128 rows. So, 128 rows of pixels are shifted from the image area into the masked storage area. These pixels are not read out for a number of (e.g., 4) frames (512/128=4). Pixels from the dark area will be shifted down to collect the next images, but the provision of a dark area is not necessary because the CCD is kept cool (−80° C.) so minimal dark current charge is generated. Method 1700 further comprises step 1720 in which a first number of (e.g., 8) buffer rows in a frame is shifted down to the register and cleared. The number 8 is arbitrarily chosen.

This number should correspond to the distance d shown in FIG. 12. Method 1700 further comprises step 1730 in which the pixels associated with the first frequency band is vertically binned and shifted. As a non-limiting example, 4 rows of pixels are associated with a frequency band, and these rows are binned and read out as one row. Method 1700 further comprises step 1740 in which at least some of the rows in the band gap bg before the next frequency band are cleared. Steps 1730 and step 1740 are thereafter repeated for each of the other frequency bands. Method 1700 further comprises step 1750 in which at least some of the buffer rows in the gap g between two rows of images 1230 are shifted and cleared. Steps 1730 through 1750 are repeated for each row of source points when the source points are arranged in an array.

FIG. 17B is a spreadsheet for estimating the throughput for system 100 using a frame transfer EMCCD as detector 1330 according to exemplary embodiments. As shown in FIG. 17B, for a frame transfer CCD having 512×512 pixels in the image area, a normal read out time of $1 \times 10^{-7}$ second, a vertical shift time of $4 \times 10^{-7}$ second, and a horizontal register clear time of $5 \times 10^{-6}$ second, using method 1700, the time to read out emission data from 4 rows of source points is about 0.00096 seconds, resulting in a readout speed higher than 1000 Hz, which is much faster than the normal readout speed of 30 Hz for the CCD. FIG. 17C is a spreadsheet for estimating the throughput for system 100 using a 1004×1002 EMCCD as detector 1330 according to exemplary embodiments. As shown in FIG. 17C, the time for reading out emission data from 4 rows of source points in this case is about 0.00113 seconds, resulting in a readout speed close to 1000 Hz.

Figure 18:
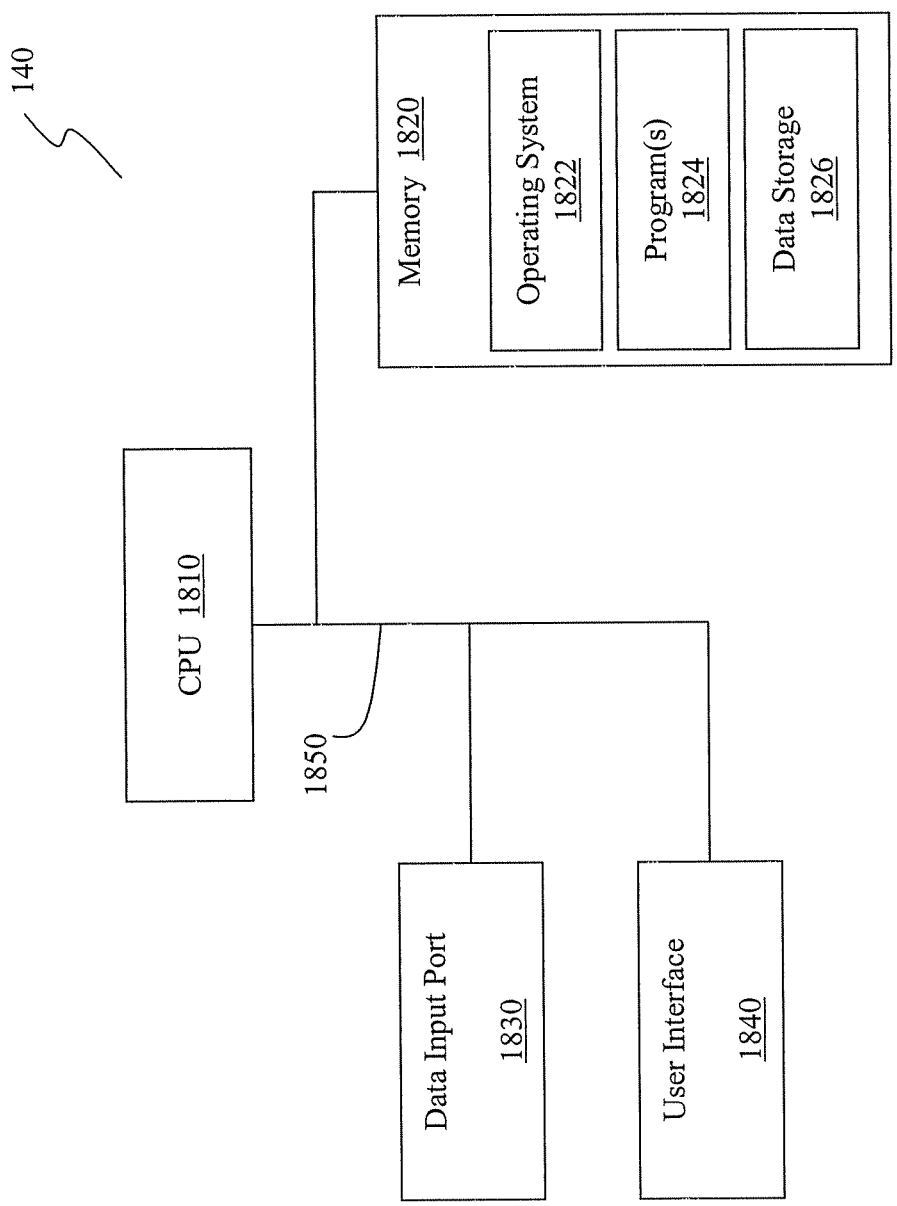
FIG. 18 is a block diagram of a computer system used in the system in FIG. 1 according to exemplary embodiments of the present teaching.

In exemplary embodiments of the present teaching, optical data collected by detector 1330 is sent to computer system 140 and optionally or additionally DSP or FPGA 150 for base determination. FIG. 18 is a block diagram of computer system 140 according to exemplary embodiments of the present teaching. As shown in FIG. 18, computer system 140 comprises a central processing unit (CPU) 1810, a memory unit 1820, a data input port 1830, and a user interface 1840, interconnected by one or more buses 1850. Memory unit 1820 preferably stores operating system software 1822 and other software programs including a program 1824 for base determination. Memory unit 1820 further comprises a data storage unit 1826 for storing optical data collected by detector 1330 and sent to computer system 140 through data input port 1830. Program 1824 comprises coded instructions, which, when executed by CPU 1810, cause computer system 140 to carry out methods for detecting light emissions from multiple source points as described above and/or methods for base determination based on the detected data according to exemplary embodiments of the present teaching, as explained in more detail below.

With the illumination of excitation light, a labeled and incorporated nucleotide should fluoresce by emitting photons from an associated source point. The spectrum of the photons collected at detector 130 from this single incorporation event should be a collection of photons with different energies or frequencies. When the number of collected photons is large, the spectrum should resemble the normal dye spectrum corresponding to the fluorescent dye used to label the incorporated nucleotide. The spectrum will vary, however, due to the small number of photons that are typically collected by detector 1330 from the single incorporation event in each collection time period.

Figure 19:
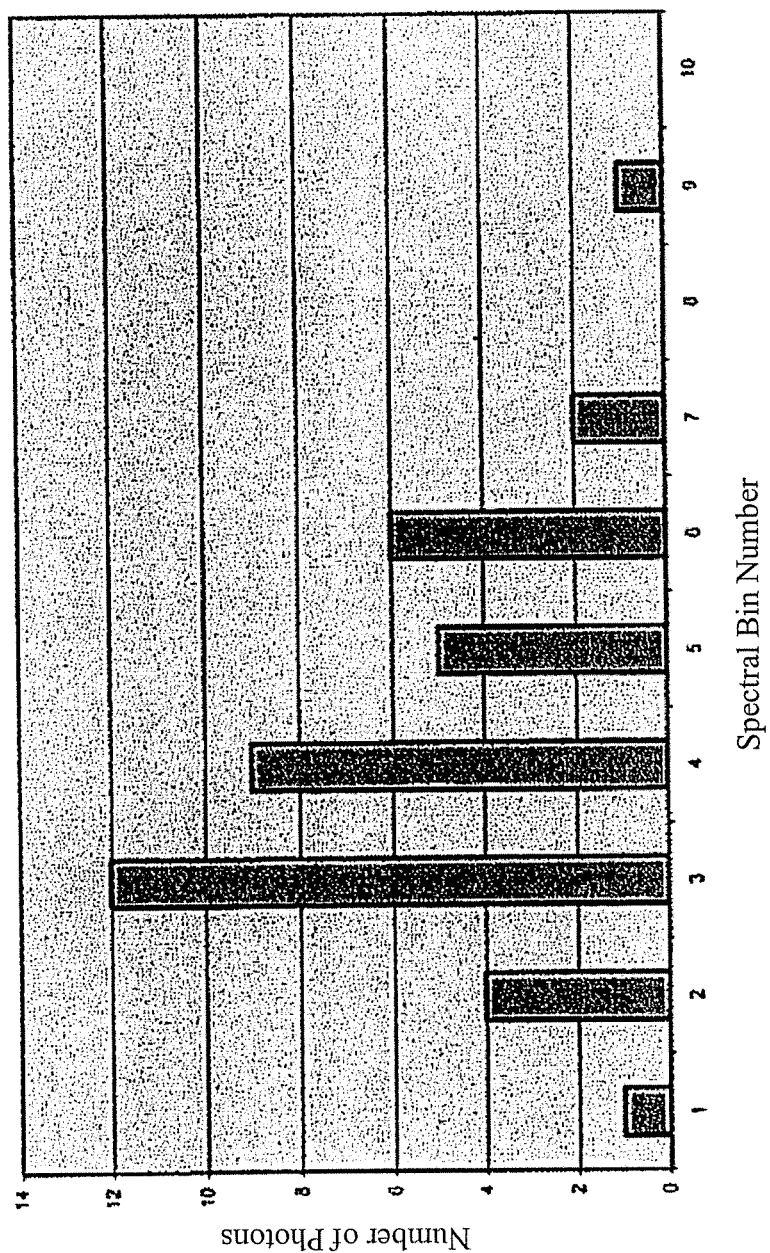
FIG. 19 is a histogram illustrating the number of photons in different spectral bins detected from a single incorporation event.

For example, a fluorescing dye may emit 10,000 photons over a 10 micro second period, and about 4% of the 10,000 photons may be detected by detector 1330 in ten time bins each corresponding to, for example, a one micro second period. Thus, roughly 40 photons may be collected in each time bin. Plotted spectrally over 10 spectral bins, the 40 expected photons might spread out like the histogram shown in FIG. 19. Because of the small number of photons, the distribution in FIG. 19 may not match the normal dye spectrum corresponding to the incorporated nucleotide, and the mismatch may lead to a chance of incorrect base determination.

Figure 20:
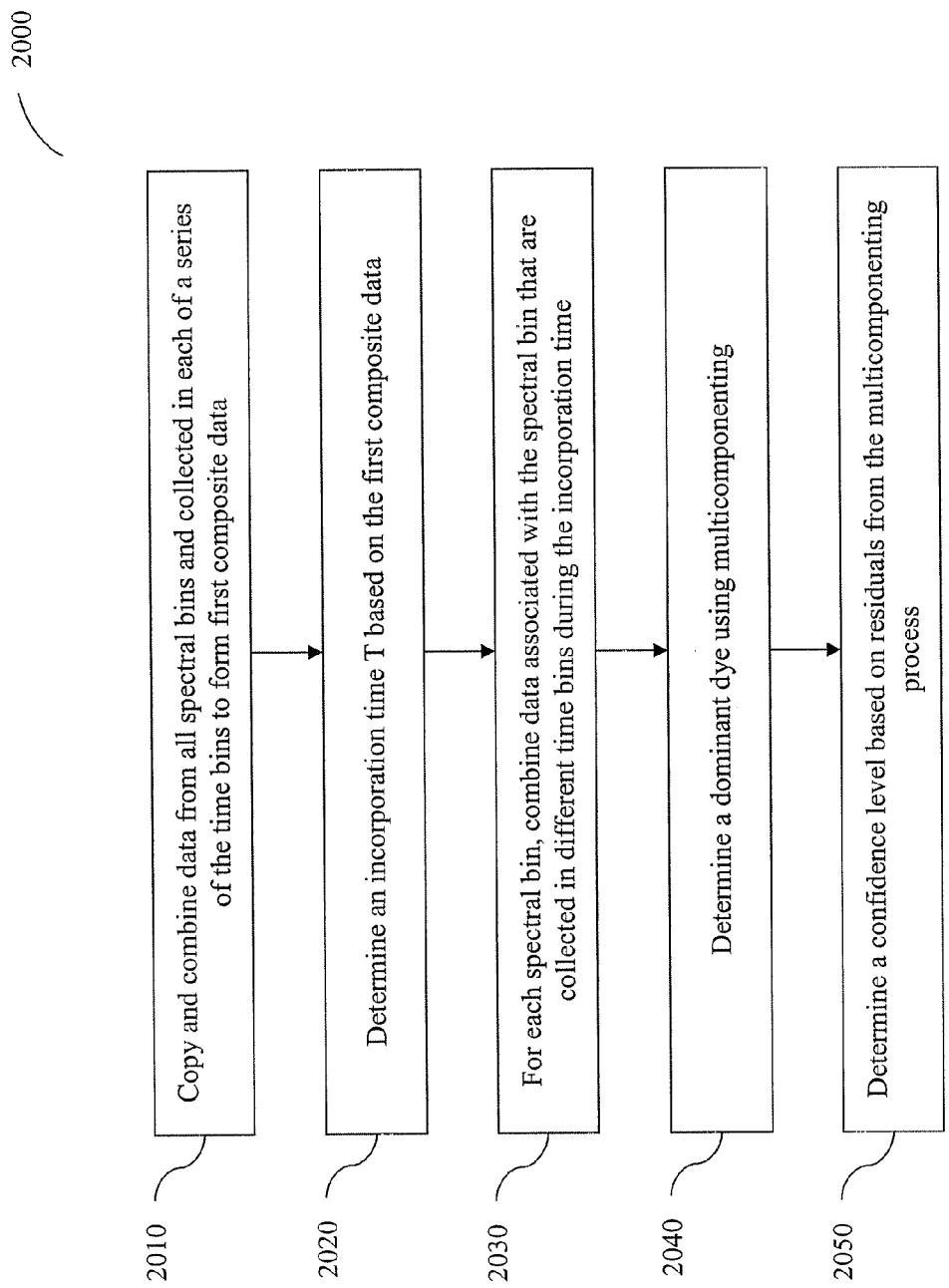
FIG. 20 is a flowchart of an exemplary embodiment of a method useful for base determination according to the present teaching.

In exemplary embodiments, to avoid a base determination problem caused by a small number of photons from a single incorporation event, the present teaching comprises a method 2000 for base determination illustrated by the flowchart in FIG. 20. As shown in FIG. 20, method 2000 comprises step 2010 in which data from all spectral bins collected in each of a plurality of consecutive time bins are copied and combined to form composite light data. Method 2000 further comprises step 2020 in which the composite data from the plurality of consecutive time bins are used to determine an incorporation time interval T.

Figure 21:
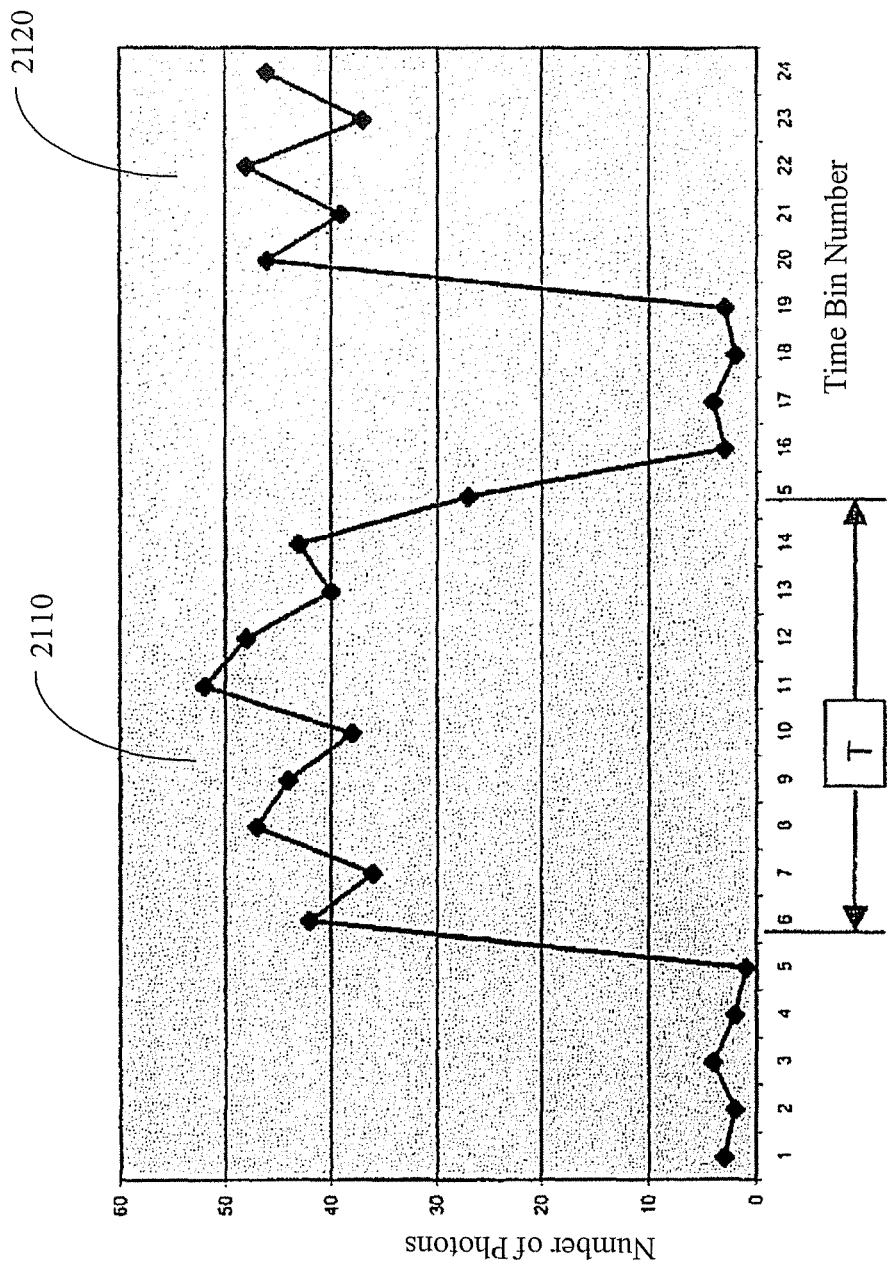
FIG. 21 is a plot of composite data over a plurality of time bins according to exemplary embodiments of the present teaching.

FIG. 21 is a plot of the composite data over a plurality of 24 time bins showing the number of photons detected in each time bin. As shown in FIG. 21, during time bins 1, 2, 3, 4, and 5, and time bins 16, 17, 18, and 19, the composite data indicate small numbers of photons coming from a background of diffusion events, trial events, and substrate fluorescence. In other time bins, the numbers of photons are significantly larger, resulting in large rises 2110 and 2120 above the background noises. Rises 2110 and 2120 indicate incorporation events. The incorporation time T for the incorporation event corresponding to rise 2110 can be determined by measuring the width of rise 2110, as shown in FIG. 21.

Since most of the photons detected during the incorporation time interval T are from a single incorporation event, for each color bin, data associated with the same spectral bin but collected in different time bins in the incorporation time interval can be combined, resulting in increased data points for the spectral bin. The increase in the number of data points leads to an improved multicomponenting process, which is used to convert color data to dye composition. Thus, method 2000 further comprises step 2030 in which data associated with each spectral bin or frequency band of interest but collected in different time bins in the incorporation time interval T are combined, and step 2040 in which the combined data is used in a conventional multicomponenting process to determine a dominant dye, which is used to determine the base being incorporated. Method 2000 further comprises step 2050 in which the residuals of the multicomponenting process is used to determine a confidence level.

Method 2000 for improving the signal to noise ratio by combining data from multiple time bins may be coded as a computer program and executed by computer system 140. Alternatively, since the same algorithm in method 2000 is executed a large number of times, hardware solutions such as field program gate arrays (FPGA) or digital signal processors (DSP) 150 and the like can be used to reduce the computation load and data stream size. The FPGAs or DSPs 150 could be integrated in detector(s) 1330, between detector 1330 and computer system 140, as shown in FIG. 1, or installed into computer system 140.

The foregoing descriptions of specific embodiments of the present teaching have been presented for purposes of illustration and description. They are not intended to be exhaustive or to limit the teaching to the precise forms disclosed, and obviously many modifications and variations are possible in light of the above teaching. The embodiments were chosen and described in order to best explain the principles of the teaching and its practical application, to thereby enable others skilled in the art to best use the teaching and various embodiments with various modifications as are suited to the particular use contemplated. It is intended that the scope of the teaching be defined by the claims appended hereto and their equivalents.

What is claimed is:

1. A method for sequencing a plurality of target nucleic acid molecules, comprising:
   delivering polymerase molecules to a plurality of spatially confined and separated source points provided within discrete cavities of a sample holder, each discrete cavity having a diameter smaller than a wavelength of an excitation light, wherein the polymerase molecules each have at least one photoactivatable linker and are secured to a nanobead by a linker, the nanobead sized to fit one bead in a cavity of the discrete cavities and deliver one polymerase molecule to the cavity;
   directing activation light to activate the photoactivatable linker and immobilize within the discrete cavities at least one polymerase molecule;
   subjecting the plurality of source points provided within the discrete cavities of the sample holder to nucleic acid polymerization reactions, wherein the source points each comprise fluorescence-labeled bases, primers, and at least a single target nucleic acid molecule, and wherein a majority of the plurality of source points each has a single polymerase molecule;
   directing the excitation light toward the sample holder at an angle off-axis with respect to a normal of the sample holder and achieving total internal reflection so that an amount of the excitation light is recycled within a substrate of the sample holder to illuminate the source points and to cause the source points to fluoresce while the discrete cavities reduce light scatter, wherein the directing excitation light further includes directing linearly polarized excitation light toward the sample holder; and
   collecting fluorescent signals from the illuminated source points and focusing the fluorescent signals onto at least one detector to form spatially resolved images of the source points on the at least one detector to determine time sequences of base incorporations in the polymerization reactions.

2. The method of claim 1 wherein the at least one detector has multiple pixel elements and an optical assembly is configured to form the spatially resolved images of the source points on the at least one detector.

3. The method of claim 1 wherein the linearly polarized excitation light further includes directing linearly polarized excitation light toward the sample holder with an electric field vector in the excitation light parallel to a plane of incidence.

4. The method of claim 1 wherein the sample holder comprises a transparent substrate and the directing excitation light comprises directing the excitation light toward the sample holder such that the excitation light enters the transparent substrate at an angle selected to cause total internal reflection when a reflected portion of the excitation light impinges upon an internal surface of the transparent substrate.

5. The method of claim 4 wherein the sample holder further comprises a transparent member in direct or fluidic contact with the transparent substrate and the directing excitation light comprises directing the excitation light toward the sample holder such that the excitation light enters the transparent substrate through the transparent member.

6. The method of claim 4 wherein the sample holder further comprises a prism, grism or grating formed on or attached to a portion of a bottom surface of the transparent substrate, and wherein the directing excitation light comprises directing the excitation light toward the sample holder such that the excitation light is coupled into the transparent substrate through the prism, grism or grating.

7. The method of claim 4 wherein the directing excitation light comprises directing the excitation light toward a side of the transparent substrate, the side having a side surface that forms an angle with a bottom surface of the transparent substrate, the bottom surface being opposite to a top surface for supporting the plurality of source points.

8. The method of claim 1 wherein the collecting and focusing fluorescent signals comprises spectrally dispersing the fluorescent signals such that each image of a source point on the at least one detector is spectrally resolved.

9. The method of claim 1 further comprising reading data associated with the images from the at least one detector, wherein reading data comprises:
   shifting and binning a first group of pixel elements associated with a first frequency band;
   shifting and clearing pixel elements between the first group of pixel elements and a second group of pixel elements associated with a second frequency band; and
   shifting and binning the second group of pixel elements.

10. The method of claim 9 further comprising shifting and clearing a group of pixel elements not having source point images formed thereon.

11. The method of claim 1 further comprising reading data associated with the images from the at least one detector and analyzing the data, wherein analyzing the data comprises:
   obtaining data associated with each source point, the data comprising a number of detected photons in each of a plurality of spectral bins and in each of a plurality of time bins;
   combining data from multiple spectral bins corresponding to each time bin to form a first composite data;
   determining an incorporation time associated with an incorporated labeled nucleotide analog according to the first composite data;
   for each spectral bin, combining data corresponding to the spectral bin and from different time bins in the incorporation time to form second composite data; and
   determining the incorporated base according to the second composite data.

12. The method of claim 1, wherein the directing of the excitation light toward the sample holder at the angle results in no excitation light reflected from the sample holder being collected with the fluorescent signals from the illuminated source points.

13. The method of claim 1, wherein the plurality of source points are each associated with a single one of the target nucleic acid molecules and a single polymerase molecule and wherein the single polymerase molecule is immobilized to a bottom portion of the discrete cavity such that light emissions other than source point florescence are substantially blocked from collection by the at least one detector.

14. A method for sequencing a plurality of target nucleic acid molecules, comprising:
   delivering nanobeads to a plurality of source points contained with discrete cavities of a sample holder, wherein the nanobeads are each attached to at least one polymerase molecule using a cleavable linker and wherein each polymerase molecule is attached to at least one photoactivatable linker, the nanobeads sized to fit one nanobead to a cavity and deliver a single polymerase molecule to the cavity;

directing activation light to activate the photoactivatable linker and immobilize at least one polymerase molecule to source points of the plurality of source points and within the discrete cavities;

chemically activating the cleavable linkers to release the nanobeads from the polymerase molecules;

subjecting the plurality of source points of the sample holder to nucleic acid polymerization reactions, wherein the source points each further comprise fluorescence-labeled bases, primers, and at least a single target nucleic acid molecule, and wherein a majority of the plurality of source points each has a single polymerase molecule;

directing excitation light toward the sample holder at an angle off-axis with respect to a normal of the sample holder such that total internal reflection occurs to illuminate the source points and to cause the source points to fluoresce, wherein the directing excitation light further includes directing linearly polarized excitation light toward the sample holder; and collecting fluorescent signals from the illuminated source points and focusing the fluorescent signals onto at least one detector to form spatially resolved images of the source points on the at least one detector to determine time sequences of base additions in the polymerization reactions.

15. The method of claim 14 wherein the at least one detector has multiple pixel elements and the optical assembly is configured to form the spatially resolved images of the source points on the at least one detector.

16. The method of claim 14 wherein each nanobead is sized such that only one nanobead occupies each discrete cavity excluding other nanobeads and immobilizing single polymerase molecules to each of the plurality of source points.

17. The method of claim 15 wherein the directing linearly polarized excitation light further includes directing linearly polarized excitation light toward the sample holder with an electric field vector in the excitation light parallel to a plane of incidence.

18. The method of claim 15 wherein the sample holder comprises a transparent substrate and the directing excitation light comprises directing the excitation light toward the sample holder such that the excitation light enters the transparent substrate at an angle selected to cause total internal reflection when a reflected portion of the excitation light impinges upon an internal surface of the transparent substrate.

19. The method of claim 18 wherein the sample holder further comprises a transparent member in direct or fluidic contact with the transparent substrate and the directing excitation light comprises directing the excitation light toward the sample holder such that the excitation light enters the transparent substrate through the transparent member.

20. The method of claim 18 wherein the sample holder further comprises a prism, grism or grating formed on or attached to a portion of a bottom surface of the transparent substrate, and wherein the directing excitation light comprises directing the excitation light toward the sample holder such that the excitation light is coupled into the transparent substrate through the prism, grism or grating.

21. The method of claim 18 wherein the directing excitation light comprises directing the excitation light through a side of the transparent substrate, the side having a side surface that forms an angle with a bottom surface of the transparent substrate, the bottom surface being opposite to a top surface for supporting the plurality of source points.

22. The method of claim 15 wherein the collecting and focusing fluorescent signals comprises spectrally dispersing the fluorescent signals such that each image of a source point on the at least one detector is spectrally resolved.

23. The method of claim 15 further comprising reading data associated with the images from the at least one detector, wherein reading data comprises:

shifting and binning a first group of pixel elements associated with a first frequency band;

shifting and clearing pixel elements between the first group of pixel elements and a second group of pixel elements associated with a second frequency band; and shifting and binning the second group of pixel elements.

24. The method of claim 23 further comprising shifting and clearing a group of pixel elements not having source point images formed thereon.

25. The method of claim 15 further comprising reading data associated with the images from the at least one detector and analyzing the data, wherein analyzing the data comprises:

obtaining data associated with each source point, the data comprising a number of detected photons in each of a plurality of spectral bins and in each of a plurality of time bins;

combining data from multiple spectral bins corresponding to each time bin to form a first composite data;

determining an incorporation time associated with an incorporated labeled nucleotide analog according to the first composite data;

for each spectral bin, combining data corresponding to the spectral bin and from different time bins in the incorporation time to form second composite data; and determining the incorporated base according to the second composite data.

26. The method of claim 14, wherein the directing of the excitation light toward the sample holder at the angle results in no excitation light reflected from the sample holder being collected with the fluorescent signals from the illuminated source points.

27. A method for sequencing a plurality of target nucleic acid molecules, comprising:

delivering to a sample holder with a plurality discrete cavities containing source points a solution containing a plurality of nanobeads linked to a plurality of target nucleic acid molecules and/or a plurality of polymerase molecules each having at least one photoactivatable linker, each nanobead sized such that only one nanobead fits in a discrete cavity, the discrete cavity having a diameter less than a wavelength of an excitation light;

directing activation light to activate the photoactivatable linker and immobilize the plurality of target nucleic acid molecules and/or polymerase molecules within discrete cavities containing source points;

removing the nanobeads;

washing the plurality of source points to remove unbound target nucleic acid molecules and/or polymerase molecules;

repeating delivery, immobilization, removing, and wash steps until a majority of the plurality of discrete cavities containing source points includes at least a single bound target nucleic acid molecule and/or a single bound polymerase molecule;

subjecting the plurality of source points to nucleic acid polymerization reactions, (1) wherein when a majority of the source points have a single bound target nucleic acid molecule, the source points each further comprise fluorescence-labeled bases, primers, and at least one polymerase molecule, (2) wherein when a majority of the source points have a single bound polymerase molecule, the source points each further comprise fluorescence-labeled bases, primers, and at least one target nucleic acid molecule; and (3) wherein when a majority of the source points have a single bound target nucleic acid molecule and a single bound molecule, the source points each further comprise fluorescence-labeled bases and primers;

directing the excitation light toward the sample holder at an angle off-axis with respect to a normal of the sample holder such that total internal reflection occurs to illuminate the source points and to cause the source points to fluoresce while the discrete cavities reduce light scatter, wherein the directing excitation light further includes directing linearly polarized excitation light toward the sample holder with an electric field vector in the excitation light parallel to a plane of incidence; and collecting fluorescent signals from the illuminated source points and focusing the fluorescent signals onto at least one detector to form spatially resolved images of the source points on the at least one detector to determine time sequences of base incorporations in the polymerization reactions.

28. The method of claim 27 wherein the at least one detector has multiple pixel elements and the optical assembly is configured to form the spatially resolved images of the source points on the at least one detector.

29. The method of claim 27 wherein the removing the nanobeads comprises dissolving the nanobeads.

* * * * *